(12) United States Patent
Errico et al.

(10) Patent No.: US 8,233,988 B2
(45) Date of Patent: *Jul. 31, 2012

(54) ELECTRICAL STIMULATION TREATMENT OF HYPOTENSION

(75) Inventors: Joseph P. Errico, Warren, NJ (US); Bruce J. Simon, Mountain Lakes, NJ (US); Steven Mendez, New York, NY (US)

(73) Assignee: ElectroCore LLC, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/232,258

(22) Filed: Sep. 14, 2011

(65) Prior Publication Data

US 2012/0065698 A1 Mar. 15, 2012

Related U.S. Application Data

(63) Continuation of application No. 12/612,177, filed on Nov. 4, 2009, now Pat. No. 8,041,428, which is a continuation-in-part of application No. 11/592,095, filed on Nov. 2, 2006, now Pat. No. 7,725,188.

(60) Provisional application No. 60/814,312, filed on Jun. 16, 2006, provisional application No. 60/772,361, filed on Feb. 10, 2006.

(51) Int. Cl.
*A61N 1/00* (2006.01)
(52) U.S. Cl. .......................................... 607/44
(58) Field of Classification Search ..................... 607/44
See application file for complete search history.

(56) References Cited

U.S. PATENT DOCUMENTS

| 3,946,745 | A | 3/1976 | Hsiang/Lai et al. |
| 3,949,743 | A | 4/1976 | Shanbrom |
| 4,305,402 | A | 12/1981 | Katims |
| 4,351,330 | A | 9/1982 | Scarberry |
| 4,503,863 | A | 3/1985 | Katims |
| 4,649,935 | A | 3/1987 | Charmillot et al. |
| 4,765,322 | A | 8/1988 | Charmillot et al. |
| 4,904,472 | A | 2/1990 | Belardinelli et al. |
| 4,945,910 | A | 8/1990 | Budyko et al. |

(Continued)

FOREIGN PATENT DOCUMENTS

WO   WO 01/89526 A1   11/2001

(Continued)

OTHER PUBLICATIONS

International Search Report and Written Opinion of the International Searching Authority dated May 20, 2009 of International Application No. PCT/US2009/038081, International filing date Mar. 24, 2009.

(Continued)

*Primary Examiner* — George Manuel
*Assistant Examiner* — Robert N Wieland
(74) *Attorney, Agent, or Firm* — John T. Raffle

(57) ABSTRACT

The present invention includes methods and devices for treating hypotension, such as in cases of shock, including septic shock, anaphylactic shock and hypovolemia. The method includes the step of applying at least one electrical impulse to at least one selected region of a parasympathetic nervous system of the patient. The electrical impulse is sufficient to modulate one or more nerves of the parasympathetic nervous system to increase the ratio of blood pressure to heart rate and relieve the condition and/or extend the patient's life.

17 Claims, 19 Drawing Sheets

U.S. PATENT DOCUMENTS

| | | | |
|---|---|---|---|
| 4,989,604 A | 2/1991 | Fang | |
| 5,054,486 A | 10/1991 | Yamada | |
| 5,107,835 A | 4/1992 | Thomas | |
| 5,109,846 A | 5/1992 | Thomas | |
| 5,123,413 A | 6/1992 | Hasegawa et al. | |
| 5,135,480 A | 8/1992 | Bannon et al. | |
| 5,152,286 A | 10/1992 | Sitko et al. | |
| 5,405,362 A | 4/1995 | Kramer et al. | |
| 5,405,366 A | 4/1995 | Fox et al. | |
| 5,454,840 A | 10/1995 | Krakovsky et al. | |
| 5,540,730 A | 7/1996 | Terry, Jr. et al. | |
| 5,620,463 A | 4/1997 | Drolet | |
| 5,658,322 A | 8/1997 | Fleming | |
| 5,690,692 A | 11/1997 | Fleming | |
| 5,707,400 A | 1/1998 | Terry, Jr. et al. | |
| 5,814,078 A | 9/1998 | Zhou et al. | |
| 5,849,026 A | 12/1998 | Zhou et al. | |
| 5,891,182 A | 4/1999 | Fleming | |
| 5,911,218 A | 6/1999 | DiMarco | |
| 5,931,806 A | 8/1999 | Shimada | |
| 5,956,501 A | 9/1999 | Brown | |
| 5,972,026 A | 10/1999 | Laufer et al. | |
| 5,995,873 A | 11/1999 | Rhodes | |
| 6,006,134 A | 12/1999 | Hill et al. | |
| 6,043,273 A | 3/2000 | Duhaylongsod | |
| 6,060,454 A | 5/2000 | Duhaylongsod | |
| 6,083,249 A | 7/2000 | Familoni | |
| 6,083,255 A | 7/2000 | Laufer et al. | |
| 6,087,394 A | 7/2000 | Duhaylongsod | |
| 6,101,412 A | 8/2000 | Duhaylongsod | |
| 6,125,301 A | 9/2000 | Capel | |
| 6,127,410 A | 10/2000 | Duhaylongsod | |
| 6,141,589 A | 10/2000 | Duhaylongsod | |
| 6,198,970 B1 | 3/2001 | Freed et al. | |
| 6,200,333 B1 | 3/2001 | Laufer | |
| 6,203,562 B1 | 3/2001 | Ohkubo | |
| 6,212,432 B1 | 4/2001 | Matsuura | |
| 6,230,052 B1 | 5/2001 | Wolff et al. | |
| 6,258,087 B1 | 7/2001 | Edwards et al. | |
| 6,273,886 B1 | 8/2001 | Edwards et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,325,798 B1 | 12/2001 | Edwards et al. | |
| 6,327,503 B1 | 12/2001 | Familoni | |
| 6,341,236 B1 | 1/2002 | Osorio et al. | |
| 6,342,221 B1 | 1/2002 | Thorpe et al. | |
| 6,347,247 B1 | 2/2002 | Dev | |
| 6,356,786 B1 | 3/2002 | Rezai et al. | |
| 6,356,787 B1 | 3/2002 | Rezai et al. | |
| 6,363,937 B1 | 4/2002 | Hovda et al. | |
| 6,366,814 B1 | 4/2002 | Boveja et al. | |
| 6,402,744 B2 | 6/2002 | Edwards et al. | |
| 6,411,852 B1 | 6/2002 | Danek et al. | |
| 6,414,018 B1 | 7/2002 | Duhaylongsod | |
| 6,423,058 B1 | 7/2002 | Edwards et al. | |
| 6,424,864 B1 | 7/2002 | Matsuura | |
| 6,438,423 B1 | 8/2002 | Rezai et al. | |
| 6,440,128 B1 | 8/2002 | Edwards et al. | |
| 6,464,697 B1 | 10/2002 | Edwards et al. | |
| 6,485,416 B1 | 11/2002 | Platt et al. | |
| 6,547,776 B1 | 4/2003 | Gaiser et al. | |
| 6,549,808 B1 | 4/2003 | Gisel et al. | |
| 6,562,034 B2 | 5/2003 | Edwards et al. | |
| 6,587,719 B1 | 7/2003 | Barrett et al. | |
| 6,609,025 B2 | 8/2003 | Barrett | |
| 6,609,030 B1 | 8/2003 | Rezai et al. | |
| 6,610,713 B2 | 8/2003 | Tracey | |
| 6,612,983 B1 | 9/2003 | Marchal | |
| 6,629,951 B2 | 10/2003 | Laufer et al. | |
| 6,633,779 B1 | 10/2003 | Schuler et al. | |
| 6,656,960 B2 | 12/2003 | Puskas | |
| 6,675,047 B1 | 1/2004 | Konoplev et al. | |
| 6,676,686 B2 | 1/2004 | Naganuma | |
| 6,681,136 B2 | 1/2004 | Schuler et al. | |
| 6,711,436 B1 | 3/2004 | Duhaylongsod | |
| 6,712,074 B2 | 3/2004 | Edwards et al. | |
| 6,738,667 B2 | 5/2004 | Deno et al. | |
| 6,752,765 B1 | 6/2004 | Jensen et al. | |
| 6,755,849 B1 | 6/2004 | Gowda et al. | |
| 6,778,854 B2 | 8/2004 | Puskas | |
| 6,819,956 B2 | 11/2004 | DiLorenzo | |
| 6,838,429 B2 | 1/2005 | Paslin | |
| 6,865,416 B2 | 3/2005 | Dev | |
| 6,871,092 B2 | 3/2005 | Piccone | |
| 6,871,099 B1 | 3/2005 | Whitehurst et al. | |
| 6,872,206 B2 | 3/2005 | Edwards et al. | |
| 6,885,888 B2 | 4/2005 | Rezai | |
| 6,913,616 B2 | 7/2005 | Hamilton et al. | |
| 6,934,583 B2 | 8/2005 | Weinberg et al. | |
| 6,937,896 B1 | 8/2005 | Kroll | |
| 6,937,903 B2 | 8/2005 | Schuler et al. | |
| 6,957,106 B2 | 10/2005 | Schuler et al. | |
| 6,961,622 B2 | 11/2005 | Gilbert | |
| 6,970,742 B2 | 11/2005 | Mann et al. | |
| 6,973,347 B1 | 12/2005 | Ben/Haim | |
| 6,974,224 B2 | 12/2005 | Thomas/Benedict | |
| 7,031,745 B2 | 4/2006 | Shen | |
| 7,072,720 B2 | 7/2006 | Puskas | |
| 7,092,755 B2 | 8/2006 | Florio | |
| 7,123,961 B1 | 10/2006 | Kroll | |
| 7,142,910 B2 | 11/2006 | Puskas | |
| 7,167,750 B2 | 1/2007 | Knudson | |
| 7,203,548 B2 | 4/2007 | Whitehurst | |
| 7,225,019 B2 | 5/2007 | Jahns | |
| 7,228,167 B2 | 6/2007 | Kara | |
| 7,292,890 B2 | 11/2007 | Whitehurst | |
| 7,310,552 B2 | 12/2007 | Puskas | |
| 7,493,161 B2 * | 2/2009 | Libbus et al. | 607/4 |
| 7,594,925 B2 * | 9/2009 | Danek et al. | 607/96 |
| 2002/0002387 A1 | 1/2002 | Naganuma | |
| 2002/0010495 A1 | 1/2002 | Freed et al. | |
| 2002/0016344 A1 | 2/2002 | Tracey | |
| 2002/0016615 A1 | 2/2002 | Dev | |
| 2002/0072738 A1 | 6/2002 | Edwards et al. | |
| 2002/0087192 A1 | 7/2002 | Barrett | |
| 2002/0091379 A1 | 7/2002 | Danek et al. | |
| 2002/0107515 A1 | 8/2002 | Edwards et al. | |
| 2002/0111386 A1 | 8/2002 | Sekins et al. | |
| 2002/0116030 A1 | 8/2002 | Rezai | |
| 2002/0143373 A1 | 10/2002 | Courtnage et al. | |
| 2002/0151888 A1 | 10/2002 | Edwards et al. | |
| 2002/0183682 A1 | 12/2002 | Darvish | |
| 2002/0198570 A1 | 12/2002 | Puskas | |
| 2002/0198571 A1 | 12/2002 | Puskas | |
| 2002/0198574 A1 | 12/2002 | Gumpert | |
| 2003/0023287 A1 | 1/2003 | Edwards et al. | |
| 2003/0074039 A1 | 4/2003 | Puskas | |
| 2003/0093128 A1 | 5/2003 | Freed et al. | |
| 2003/0144572 A1 | 7/2003 | Oschman et al. | |
| 2003/0181949 A1 | 9/2003 | Whale | |
| 2003/0216791 A1 | 11/2003 | Schuler et al. | |
| 2003/0216792 A1 | 11/2003 | Levin et al. | |
| 2003/0233099 A1 | 12/2003 | Danaek et al. | |
| 2004/0010289 A1 | 1/2004 | Biggs et al. | |
| 2004/0029849 A1 | 2/2004 | Schatzberg et al. | |
| 2004/0030368 A1 | 2/2004 | Kemeny et al. | |
| 2004/0044390 A1 | 3/2004 | Szeles | |
| 2004/0059383 A1 | 3/2004 | Puskas | |
| 2004/0073278 A1 | 4/2004 | Pachys | |
| 2004/0088030 A1 | 5/2004 | Jung, Jr. | |
| 2004/0088036 A1 | 5/2004 | Gilbert | |
| 2004/0106954 A1 | 6/2004 | Whitehurst et al. | |
| 2004/0116981 A1 | 6/2004 | Mazar | |
| 2004/0122488 A1 | 6/2004 | Mazar et al. | |
| 2004/0122489 A1 | 6/2004 | Mazar et al. | |
| 2004/0127942 A1 | 7/2004 | Yomtov et al. | |
| 2004/0127958 A1 | 7/2004 | Mazar et al. | |
| 2004/0147969 A1 | 7/2004 | Mann et al. | |
| 2004/0147988 A1 | 7/2004 | Stephens | |
| 2004/0162597 A1 | 8/2004 | Hamilton et al. | |
| 2004/0167580 A1 | 8/2004 | Mann et al. | |
| 2004/0172075 A1 | 9/2004 | Shafer et al. | |
| 2004/0172080 A1 | 9/2004 | Stadler et al. | |
| 2004/0172084 A1 | 9/2004 | Knudson et al. | |
| 2004/0176803 A1 | 9/2004 | Whelan et al. | |

| | | |
|---|---|---|
| 2004/0176805 A1 | 9/2004 | Whelan et al. |
| 2004/0204747 A1 | 10/2004 | Kemeny et al. |
| 2004/0215289 A1 | 10/2004 | Fukui |
| 2004/0220621 A1 | 11/2004 | Zhou et al. |
| 2004/0230251 A1 | 11/2004 | Schuler et al. |
| 2004/0230252 A1 | 11/2004 | Kullok et al. |
| 2004/0249416 A1 | 12/2004 | Yun et al. |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0021092 A1 | 1/2005 | Yun et al. |
| 2005/0059153 A1 | 3/2005 | George et al. |
| 2005/0065553 A1 | 3/2005 | Ben Ezra et al. |
| 2005/0065562 A1 | 3/2005 | Rezai |
| 2005/0065567 A1 | 3/2005 | Lee et al. |
| 2005/0065573 A1 | 3/2005 | Rezai |
| 2005/0065574 A1 | 3/2005 | Rezai |
| 2005/0075701 A1 | 4/2005 | Shafer |
| 2005/0075702 A1 | 4/2005 | Shafer |
| 2005/0076909 A1 | 4/2005 | Stahmann et al. |
| 2005/0080461 A1 | 4/2005 | Stahmann et al. |
| 2005/0090722 A1 | 4/2005 | Perez |
| 2005/0107829 A1 | 5/2005 | Edwards et al. |
| 2005/0125044 A1 | 6/2005 | Tracey |
| 2005/0143788 A1 | 6/2005 | Yun et al. |
| 2005/0149146 A1 | 7/2005 | Boveja et al. |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171575 A1 | 8/2005 | Dev |
| 2005/0177192 A1 | 8/2005 | Rezai et al. |
| 2005/0182288 A1 | 8/2005 | Zabara |
| 2005/0182463 A1 | 8/2005 | Hunter |
| 2005/0187579 A1 | 8/2005 | Danek et al. |
| 2005/0187581 A1 | 8/2005 | Hara |
| 2005/0216062 A1 | 9/2005 | Herbst |
| 2005/0222628 A1 | 10/2005 | Krakousky |
| 2005/0222635 A1 | 10/2005 | Krakovsky |
| 2005/0222651 A1 | 10/2005 | Jung, Jr. |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240241 A1 | 10/2005 | Yun et al. |
| 2005/0245992 A1 | 11/2005 | Persen et al. |
| 2005/0251213 A1 | 11/2005 | Freeman |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0095079 A1 | 5/2006 | Gerber |
| 2006/0129216 A1 | 6/2006 | Hastings |
| 2006/0135998 A1 | 6/2006 | Libbus et al. |
| 2006/0167498 A1 | 7/2006 | DiLorenzo |
| 2006/0178703 A1 | 8/2006 | Huston |
| 2006/0200219 A1 | 9/2006 | Thrope |
| 2006/0229677 A1 | 10/2006 | Moffitt |
| 2006/0259107 A1 | 11/2006 | Caparso |
| 2006/0282145 A1 | 12/2006 | Caparso |
| 2006/0287679 A1 | 12/2006 | Stone |
| 2007/0027483 A1 | 2/2007 | Maschino |
| 2007/0027496 A1 | 2/2007 | Parnis et al. |
| 2007/0060954 A1 | 3/2007 | Cameron |
| 2007/0093870 A1 | 4/2007 | Maschino |
| 2007/0106337 A1 | 5/2007 | Errico |
| 2007/0106338 A1 | 5/2007 | Errico |
| 2007/0106339 A1 | 5/2007 | Errico et al. |
| 2007/0135846 A1 | 6/2007 | Knudson |
| 2007/0150006 A1 | 6/2007 | Libbus |
| 2007/0156182 A1 | 7/2007 | Castel |
| 2007/0191902 A1 | 8/2007 | Errico et al. |
| 2007/0225768 A1 | 9/2007 | Dobak, III |
| 2007/0239210 A1 | 10/2007 | Libbus |
| 2007/0250119 A1 | 10/2007 | Tyler |
| 2007/0299476 A1 | 12/2007 | Park |
| 2008/0004672 A1 | 1/2008 | Dalal |
| 2008/0183248 A1 | 7/2008 | Rezai et al. |

FOREIGN PATENT DOCUMENTS

WO    WO 2004/078252 A2    9/2004

OTHER PUBLICATIONS

International Search Report and Written Opinion of the International Searching Authority dated Jan. 29, 2008 of International Application No. PCT/US06/42752, International filing date Nov. 1, 2006.

International Search Report and Written Opinion of the International Searching Authority dated Mar. 16, 2007 of International Application No. PCT/US2006/042823, International filing date Nov. 2, 2006.

International Search Report and Written Opinion of the International Searching Authority dated Sep. 17, 2007 of International Application No. PCT/US2006/042828, International filing date Nov. 2, 2006.

Guarini et al., "Efferent Vagal Fibre Stimulation Blunts Nuclear Factor/kB Activation and Protects Against Hypovolemic Hemorrhagic Shock", Circulation 2003 vol. 107 pp. 1189/1194.

Supplemental European Search Report for EP Application No. 06827343, Aug. 21, 2009.

Supplemental European Search Report for EP Application No. 06827386.1, Aug. 21, 2009.

U.S. Appl. No. 60/206,364, Title: Vagus Nerve Stimulation Attenuation of the Systemic Inflammatory Response to Endotoxin, Filing Date: May 23, 2000, Inventor: Tracey.

\* cited by examiner

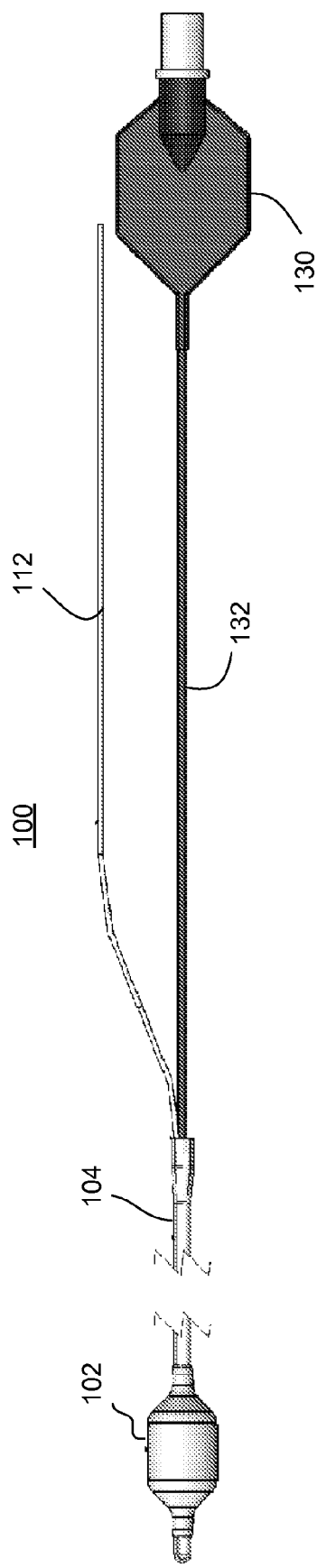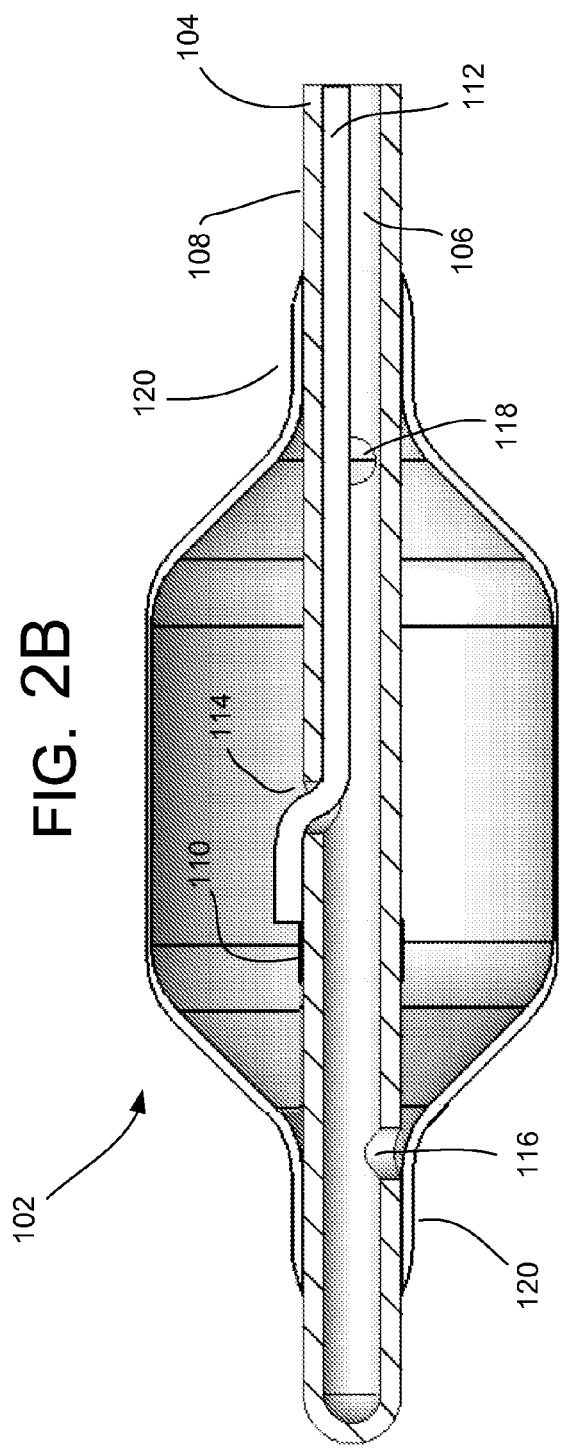

ELECTRICAL STIMULATION TREATMENT OF HYPOTENSION

CROSS REFERENCE TO RELATED APPLICATIONS

This application is a continuation of U.S. patent application Ser. No. 12/612,177, filed Nov. 4, 2009 which is a continuation-in-part of U.S. patent application Ser. No. 11/592,095 filed Nov. 2, 2006, which claims priority to U.S. Provisional Patent Application Nos. 60/814,312, filed Jun. 16, 2006 and 60/772,361, filed Feb. 10, 2006, the entire disclosures of which are hereby incorporated by reference.

BACKGROUND OF THE INVENTION

The present invention relates to the field of delivery of electrical impulses to bodily tissues for therapeutic purposes, and more specifically to devices and methods for treating conditions associated with hypotension.

There are a number of treatments for various infirmities that require the destruction of otherwise healthy tissue in order to produce a beneficial effect. Malfunctioning tissue is identified, and then lesioned or otherwise compromised, rather than attempting to repair the tissue to its normal functionality. While there are a variety of different techniques and mechanisms that have been designed to focus lesioning directly onto the target nerve tissue, collateral damage is inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant. For example, at least one popular diet pill of the late 1990's was subsequently found to cause heart attacks and strokes. Thus, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments. Moreover, unlike surgery and medicine, electrical stimulation is generally a wholly reversible and non-destructive treatment.

Blood pressure is the pressure exerted by the blood on the walls of the blood vessels. Unless indicated otherwise, blood pressure refers to systemic arterial blood pressure, i.e., the pressure in the large arteries delivering blood to body parts other than the lungs, such as the brachial artery in the arm. The pressure of the blood in other vessels is lower than the arterial pressure. Blood pressure values are universally stated in millimetres of mercury (mm Hg), and are always given relative to atmospheric pressure. For example, the absolute pressure of the blood in an artery with mean arterial pressure stated as 100 mm Hg, on a day with atmospheric pressure of 760 mm Hg, is 860 mm Hg.

The systolic pressure is defined as the peak pressure in the arteries during the cardiac cycle; the diastolic pressure is the lowest pressure (at the resting phase of the cardiac cycle). The mean arterial pressure and pulse pressure are other important quantities. Typical values for a resting, healthy adult are approximately 120 mm Hg systolic and 80 mm Hg diastolic (written as 120/80 mm Hg), with large individual variations. These measures of blood pressure are not static, but undergo natural variations from one heartbeat to another or throughout the day (in a circadian rhythm); they also change in response to stress, nutritional factors, drugs, or disease.

Blood pressure that is too low is known as hypotension. Low blood pressure may be a sign of severe disease and requires urgent medical attention. When blood pressure and blood flow are very low, the perfusion of the brain may be critically decreased (i.e., the blood supply is not sufficient), causing lightheadedness, dizziness, weakness and fainting.

Sometimes the blood pressure drops significantly when a patient stands up from sitting. This is known as orthostatic hypotension. In this disorder, gravity reduces the rate of blood return from the veins below the heart back to the heart, thus reducing stroke volume and cardiac output. When people are healthy, they quickly constrict the veins below the heart and increase their heart rate to minimize and compensate for the gravity effect. This is done at a subconscious level via the autonomic nervous system. The system usually requires a few seconds to fully adjust and if the compensations are too slow or inadequate, the individual will suffer reduced blood flow to the brain, dizziness and potential blackout. Increases in G-loading, such as routinely experienced by supersonic jet pilots "pulling Gs", greatly increases this effect. Repositioning the body perpendicular to gravity largely eliminates the problem.

Hypotension often accompanies and complicates many other systemic health problems, such as anaphylaxis, hypovolemia and sepsis, leading to anaphylactic shock, hypovolemic shock and septic shock, making it more difficult to address the underlying health problem. For example, U.S. Patent Application Number 20050065553, Ben Ezra, et al., titled, "Applications of vagal stimulation," which is incorporated in its entirety by reference, proposes a method to treat a patient's sepsis by applying an appropriately configured current to the vagus nerve. However, when accompanied with refractory arterial hypotension, sepsis becomes septic shock.

Septic shock is a serious medical condition causing such effects as multiple organ failure and death in response to infection and sepsis. Its most common victims are children and the elderly, as their immune systems cannot cope with the infection as well as those of full-grown adults, as well as immunocompromised individuals. The mortality rate from septic shock is approximately 50%. Other various shock conditions include: systemic inflammatory response syndrome, toxic shock syndrome, adrenal insufficiency, and anaphylaxis.

A subclass of distributive shock, septic shock refers specifically to decreased tissue perfusion resulting in end-organ dysfunction. Cytokines TNFα, IL-1β, IL-6 released in a large scale inflammatory response may result in massive vasodilation, increased capillary permeability, decreased systemic vascular resistance, and hypotension. Hypotension reduces tissue perfusion pressure, and thus tissue hypoxia ensues. Finally, in an attempt to offset decreased blood pressure, ventricular dilatation and myocardial dysfunction will occur.

Another class of shock that results in systemic hypotension is hypovolemic shock. This disorder usually results from acute blood loss such as massive blood loss from bleeding in the GI tract, internal or external hemorrhage (accidental or surgical trauma), or from any condition that reduces circulating intravascular plasma volume or other body fluids such as in severe burns. In hypovolemic shock, reduced intravascular blood volume causes circulatory dysfunction and inadequate tissue perfusion. Without sufficient blood or fluid replacement, hypovolemic shock syndrome may lead to irreversible cerebral and renal damage, cardiac arrest and, ultimately, death.

Accordingly, there is a need in the art for new products and methods for treating the immediate symptoms of hypotension and shock.

SUMMARY OF THE INVENTION

The present invention involves products and methods of treatment of hypotension utilizing an electrical signal sufficient to elevate blood pressure and/or increase the ratio of blood pressure to heart rate in a patient. The present invention also encompasses treatment of pathologies causing hypotension, both chronic and acute hypotension, such as in patients with thyroid pathologies and those suffering from septic or hypovolemic shock. This treatment of hypotension may accompany treatment for other conditions, such as bronchial constriction, that also may occur in situations of shock.

In a first embodiment, a method of treating hypotension in a patient includes applying at least one electrical impulse to at least one selected region of a parasympathetic nervous system of the patient. The electrical impulse is sufficient to modulate one or more nerves of the parasympathetic nervous system such that the ratio of blood pressure to heart rate is increased. In some cases, the blood pressure will be increased without a corresponding increase in heart rate (i.e., at substantially the same heart rate). In other cases, the blood pressure will be maintained (or inhibited from dropping due to the patient's condition) at a lower heart rate than would otherwise be necessary without stimulation.

Preferably, the electrical impulse is sufficient to stimulate or activate the afferent nerves of the selected region of the parasympathetic nervous system. The stimulated afferent nerves in turn lead to a sympathetic response. Specifically, the afferent nerves cause an increase in activity of one or more nerves of the sympathetic nervous system to increase the ratio of blood pressure to heart rate in the patient. This increase in activity in the sympathetic nervous system leads to a response that ameliorates the patient's condition. This response may either be a systemic or global response on the part of the sympathetic nervous system or it may be a localized response that directly affects the patient's blood pressure.

The method further includes introducing one or more electrodes to a target site adjacent to or in close proximity to the selected region of the parasympathetic nervous system. Preferably, the target site is selected such that the signal at the selected region is strong enough to effectively stimulate the afferent nerves of the parasympathetic nervous system and weak or low enough to avoid substantial modulation of the efferent nerves of the parasympathetic nervous system at the selected region. Applicant has made the surprising discovery that, under certain optimal conditions, the afferent nerves of the parasympathetic system can be stimulated at signal levels below that required to stimulate the corresponding efferent nerves. This allows for selective stimulation of the afferent nerves in the parasympathetic nervous system.

In a preferred embodiment, the position of the electrode relative to the target site, the material and surface geometry of the electrode(s) and the amplitude of the signal are selected in combination to provide the optimal conditions for a selective signal at the target region of the parasympathetic nervous system. This selective signal is sufficient to stimulate the afferent nerves and insufficient to substantially modulate the efferent nerves in the selected region.

In an exemplary embodiment, the electrode(s) are positioned at or near (i.e., within 1-10 mm of) the cricoid cartilage of the patient and the voltage of the signal is less than about 12 volts, preferably between about 2-12 volts. In this embodiment, the electrode is enclosed within a balloon inflated with conductive fluid such that a virtual "electrode" is created having a substantially spherical shape of about 1-5 cm, preferably about 2-3 cm, in diameter.

In a second aspect of the invention, a method for treating a patient suffering from systemic hypotension includes the steps of positioning an electrode adjacent to or near a cricoid cartilage of the patient and applying an electrical impulse to the electrode. In this embodiment, the electrical impulse is sufficient to increase the ratio of blood pressure to heart rate and thus inhibit a drop in blood pressure associated with the systemic hypotension of the patient. In some cases, the blood pressure is maintained at a lower heart rate than would otherwise be necessary due to the patient's condition. In other cases, the blood pressure is increased at a substantially stable heart rate. Applicant has discovered that an appropriate electrical signal applied at a very precise target location within or adjacent to the cricoid cartilage will inhibit the drop in blood pressure associated with systemic hypotension. In addition, this signal will increase the survival time of the patient to allow the patient to receive other medical attention that may save the patient's life.

In a third aspect of the invention, a method for treating a patient suffering from hypovolemia or hypovolemic shock comprises applying an electrical impulse to the patient sufficient to keep the patient alive for an extended period of time. Applicant has discovered that an appropriate electrical signal, delivered at an appropriate location on the patient, will allow a patient undergoing hypovolemic shock to stay alive longer than he/she otherwise would without such treatment. This gives the physician time to perform other life saving steps that may allow the patient to recover from the shock.

In this embodiment, the electrical signal is also sufficient to increase the ratio of blood pressure to heart rate and thus inhibit a drop in blood pressure associated with the hypovolemic shock. The electrical impulse is preferably applied to an electrode at a target region in or on the neck of the patient. In an exemplary embodiment, the target region is in or around the cricoid cartilage.

In a preferred embodiment, the electrode is introduced through an esophagus of the patient to the target site within the neck. Once in position at the target site, the electrode is expanded to substantially contact the esophageal tissue around the target site. In one embodiment, the electrode is expanded by inflating the electrode with a fluid, such as saline or the like. In another embodiment, the electrode is housed within an enclosure and the enclosure is inflated to contact tissue at the target site. The enclosure is preferably inflated with an electrically conductive fluid that electrically couples the electrode with at least a portion of the outer wall of the enclosure.

In another embodiment, the electrode is introduced through a trachea of the patient to the target site within the neck. Preferably, the system comprises a series of annular electrodes spaced from each other on the outer surface of an endotracheal tube. The electrodes are introduced through the trachea and positioned at the target site. The electrodes may have an alternative polarity such that the current passes between electrodes or the system may include a return electrode placed on the outer surface of the patient's skin. In this latter embodiment, the annular electrodes may all have the same polarity and can be used to select the appropriate location for delivering the electrical impulse to the patient.

In a fourth aspect of the invention, a method for treating a patient suffering from sepsis or septic shock comprises applying an electrical impulse to the patient sufficient to keep the patient alive for an extended period of time. Similar to hypovolemia, applicant has discovered that an appropriate electrical signal, delivered at an appropriate location on the patient, will allow a patient undergoing septic shock to stay alive longer than he/she otherwise would without such treatment. This gives the physician time to perform other life saving steps that may allow the patient to recover from the sepsis.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims of an issued utility application.

FIG. 2A is a schematic view of an esophageal electrode device in accordance with one or more aspects of the present invention;

FIG. 2B is a cross-sectional view taken through the balloon of the esophageal electrode device of FIG. 2A;

DETAILED DESCRIPTION OF THE PREFERRED EMBODIMENT

Figure 1:
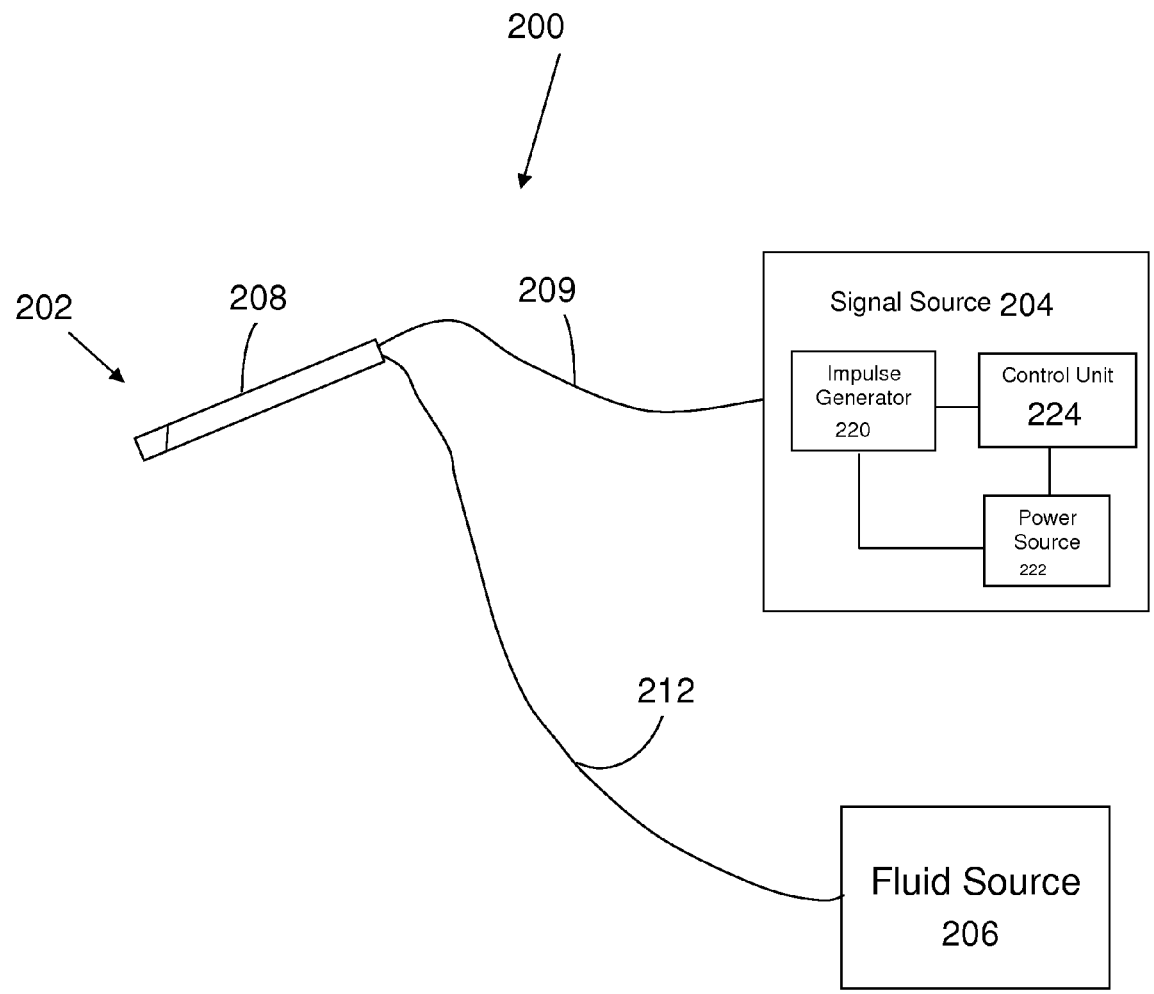
FIG. 1 is a schematic view of a nerve modulation system according to the present invention.

In the present invention, electrical energy is applied to one or more electrodes to deliver an electromagnetic field to a patient. The invention is particularly useful for applying electrical impulses that interact with the signals of one or more nerves or muscles to increase blood pressure, increase the ratio of blood pressure to heart rate and/or inhibit a blood pressure drop in a patient suffering from chronic or acute hypotension, such as orthostatic hypotension, and/or systemic hypotension that may be associated with sepsis, septic shock, hypovolemia, hypovolemic shock or any other ailment associated with, causing or caused by reduced blood pressure. For convenience, the remaining disclosure will be directed specifically to the treatment of nerves at a target region within the neck of a patient with a device introduced through the patient's esophagus and/or trachea, but it will be appreciated by those skilled in the art that the systems and methods of the present invention can be applied equally well to other tissues and nerves of the body, including but not limited to other parasympathetic nerves, sympathetic nerves, spinal or cranial nerves, e.g., optic nerve, facial nerves, enteric nerves, vestibulocochlear nerves and the like. In addition, it will be appreciated that the present invention is not limited to methods and devices that are introduced through a natural orifice in the patient and may include other means for applying the electrical impulse to the target site, such as percutaneous introduction of electrodes, transcutaneous application of energy and the like.

It has been observed in the literature that the nervous system maintains a balance of the signals carried by the sympathetic and parasympathetic nerves. The parasympathetic nervous system is thought to provide a baseline level of tonicity in the cardiac muscles in order to prevent the tissue from expanding too much, and thus is considered responsible for depressing blood pressure to prevent heart exhaustion and dangerous hypertension during extreme exertion. The sympathetic nervous system carries the opposing signals that tend to speed up the heart rate, as well as open the bronchial passages. It should be recognized that the signals of the parasympathetic nerves mediate a response similar to that of histamine, while the sympathetic signals generate an effect similar to epinephrine.

In mammals, two vagal components of the parasympathetic nervous system have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguous and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus nerve innervates ganglionic neurons which are located in or adjacent to each target organ. The VVC appears only in mammals and is associated with positive as well as negative regulation of heart rate, bronchial constriction, vocalization and contraction of the facial muscles in relation to emotional states. Generally speaking, this portion of the vagus nerve regulates parasympathetic tone. Muscle tone (also known as residual muscle tension) is the continuous and passive partial contraction of the muscles. The VVC inhibition is released (turned off) in states of alertness. This in turn causes cardiac vagal tone to decrease and heart function to increase, and airways to open, to support responses to environmental challenges.

The parasympathetic tone is balanced in part by sympathetic innervation, which generally speaking supplies signals tending to expand the myocardium (and/or effect vasoconstriction), and/or to relax the bronchial muscles, so that over-contraction and over-constriction, respectively, do not occur. Overall, myocardium tone, vasodilation, vasoconstriction, and/or airway smooth muscle tone are dependent on several factors, including parasympathetic input, inhibitory influence of circulating epinephrine, NANC inhibitory nerves and sympathetic innervation of the parasympathetic ganglia. Stimulation of the vagus nerve (up-regulation of tone), such as may occur in shock, results in a heart rate decrease and airway constriction. In this context, up-regulation is the process by which the specific effect is increased, whereas down-regulation involves a decrease of the effect. In general, the pathology of shock appears to be mediated by inflammatory cytokines that overwhelm receptors on the nerve cells and cause the cells to massively up-regulate the parasympathetic tone. On a cellular level, up-regulation is the process by which a cell increases the number of receptors to a given hormone or neurotransmitter to improve its sensitivity to this molecule. A decrease of receptors is called down-regulation.

For instance, sepsis is mediated by severe infection and may result in a large scale inflammatory response that releases cytokines TNFα, IL-1β, IL-6 mediating massive vasodilation, increased capillary permeability, decreased systemic vascular resistance, and hypotension. By comparison, anaphylaxis appears to be mediated predominantly by the hypersensitivity to an allergen causing the massive overproduction of cholenergic receptor activating cytokines that overdrive the otherwise normally operating vagus nerve to signal massive constriction of the airways. Hypovolemic shock usually results from acute blood loss such as massive blood loss from bleeding in the GI tract, internal or external hemorrhage (accidental or surgical trauma), or from any condition that reduces circulating intravascular plasma volume or other body fluids such as in severe burns. Drugs such as epinephrine drive heart rate up while also relaxing the bronchial muscles, effecting temporary relief of symptoms from these conditions.

In accordance with at least one aspect of the present invention, a method for treating a patient suffering from acute or chronic hypotension, such as orthostatic hypotension or hypotension associated with shock, includes the delivery of an electrical impulse sufficient to modulate signals in the parasympathetic nervous system (e.g., the vagus nerve). The unique signal and placement of such signal according to the invention will result in raising the heart function, and thus increasing the ratio of blood pressure to heart rate, and depending on the placement of the impulse, relaxation of the bronchi smooth muscle, dilating airways.

In preferred embodiments, the electrical impulse is sufficient to stimulate or activate one or more afferent nerves of the parasympathetic nervous system to increase the ratio of blood pressure to heart rate. Preferably, the electrical impulse is insufficient to substantially modulate the efferent nerves of the parasympathetic nervous system. The stimulated afferent nerves in turn lead to a sympathetic response. Specifically, the afferent nerves cause an increase in activity of one or more nerves of the sympathetic nervous system to increase the ratio of blood pressure to heart rate in the patient. In other embodiments, the sympathetic nervous system may be stimulated directly with electrical impulses.

In accordance with at least one aspect of the present invention, modulating the sympathetic nervous system (either directly or indirectly through the afferent branches of the parasympathetic nervous system) provides an immediate emergency response, much like a defibrillator, in situations of shock, providing an immediate increase of heart function. Moreover, the teachings of the present invention permit an immediate heart function increase to enable subsequent life saving measures that otherwise would be ineffective or impossible due to other physiological effects. Treatment in accordance with the present invention provides increased heart function, and optionally bronchodilation, for a long enough period of time so that administered medication such as epinephrine has time to take effect before the patient suffers hypoxia.

In certain embodiments, one or more electrical impulse emitting devices or electrodes may be implanted in one or more selected regions of the patient's body. Implantable devices may be useful in patients known to be subject to hypotension, such as anaphylactic shock or orthostatic hypotension. The electrodes may be powered and/or recharged from outside the body or they may have their own power source implanted within the body. By way of example, the electrodes and power source may be purchased commercially and may be programmed with a physician programmer, such as a Model 7432 also available from Medtronic, Inc.

In other embodiments, the device may be introduced to the target site minimally invasively for acute, emergency applications. For example, the electrode(s) may be introduced through a percutaneous penetration in the patient's neck as described in co-pending commonly-assigned U.S. patent application Ser. No. 12/422,483, already incorporated herein by reference. Alternatively, the electrical impulse may be delivered transcutaneously to the target site as described in co-pending, commonly-assigned U.S. patent application Ser. No. 12/469,397, also already incorporated herein by reference. In yet other embodiments, the electrodes may be introduced through a natural orifice such as the esophagus or trachea as described more fully below and in co-pending, commonly assigned U.S. patent application Ser. No. 12/394,972 and as discussed in more detail below.

Regardless of the approach used to introduce the electrodes, they will be positioned at a target site adjacent to or in close proximity to the selected region of the parasympathetic nervous system. Preferably, the optimal conditions will be selected such that the electrical impulse at the selected region is strong enough to effectively stimulate the afferent nerves of the parasympathetic nervous system and weak or low enough to avoid substantial modulation of the efferent nerves at the selected region. Applicant has made the surprising discovery that the afferent nerves of the parasympathetic can be stimulated at signal strength levels below that required to stimulate the efferent nerves. This allows for selective stimulation of the afferent nerves.

In a preferred embodiment, the target site for the electrode, the amplitude of the signal and the material and surface geometry of the electrode(s) are selected in combination to provide a signal that will stimulate the afferent nerves without stimulating the efferent nerves at the target region. In an exemplary embodiment, the electrode is positioned at or near the cricoid cartilage of the patient (i.e., with 1-10 mm, preferably within about 1-5 mm) and the voltage of the signal is less than about 12 volts, preferably between about 2-12 volts. In this embodiment, the electrode(s) are positioned within either the esophagus or the trachea of the patient such that they are spaced away from the target nerve(s) by about 5 to 20 mm. Exemplary materials and surface geometries for these electrodes are discussed in detail below.

Of course, it will be recognized that other combinations of variables can be selected to create the optimal conditions for selective stimulation of the afferent nerves. For example, electrode(s) having the same configuration as described above can be positioned further away from the target site at a higher amplitude or the electrode(s) can be positioned close to the target site at a lower amplitude.

Alternatively, the electrode can have a different design to modify the material and/or surface geometry of the electrode(s) to thereby modify the electric field gradient at the electrode and the strength of the signal at the target site. For example, electrode material and surface geometries can be selected to promote high electric field intensities and associated current densities that will drive a higher electric field gradient and a higher strength signal to the target site. This will allow for either a lower amplitude and/or an electrode position further away from the target site. Conversely, the electrode material and surface geometries can be selected to reduce or lower the electric field gradient around the electrode. In this case, the electrode position would be close to the target site and/or a higher amplitude will be selected.

To promote higher electric field gradients, surface geometries can be modified with electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. Alternatively, material can be removed at closely spaced intervals along the length of the electrode to form transverse grooves, slots, threads or the like along the electrode. Additionally or alternatively, th electrode surface (s) may be modified through chemical, electrochemical or abrasive methods to create a multiplicity of surface asperities on the electrode surface. These surface asperities will promote high electric field intensities and associated electric field gradients between the electrode surface(s) and the target site.

The electrical impulse will have a frequency between about 1 Hz to 3000 Hz, preferably between about 10 Hz to 35 Hz, and may be one or more of a full or partial sinusoid, square wave, rectangular wave, and/or triangle wave. The electrical impulse may have a pulsed on-time of between about 50 to 500 microseconds, preferably between about 100 to 400 microseconds. The polarity of the pulses may be maintained either positive or negative. Alternatively, the polarity of the pulses may be positive for some periods of the wave and negative for some other periods of the wave. By way of example, the polarity of the pulses may be altered about every second.

Referring to the drawings in detail, wherein like numerals indicate like elements, FIG. 1 schematically illustrates an exemplary nerve modulation system 200 according to the present invention. System 200 comprises an electrode 202 coupled to an electrical signal generator or source 204 for providing an electrical impulse to a target tissue. Electrode 202 (which is shown only in schematic form in FIG. 1) includes an elongated shaft or connector 208 which may be flexible or rigid, with flexible shafts optionally including support cannulas or other structures (not shown). In certain embodiments, system 200 will also include a fluid source 206 for supplying fluid to the electrode 202. Electrode shaft 208 is coupled to fluid source 204 via a fluid tube 212 and to electrical source 204 through electrical connector 209. System 200 may also include a return electrode (not shown) adapted for placement on the outer surface of the patient's skin (e.g., the back or buttocks) such that the electrical current passes through the target site and the patient's body to the return electrode. Alternatively, electrode 202 may include both the anode and cathode such that the electrical current is confined to the target site. In some embodiments, electrode 202 will include multiple electrodes (not shown) that can be alternatively turned on and off to apply the electrical impulse to different parts of the electrode 202.

Electrical source 204 may be tailored for the treatment of a particular ailment and may include an electrical impulse generator 220, a power source 222 coupled to the electrical impulse generator 220, and a control unit 224 in communication with the electrical impulse generator 220 and the power source 222. The electrodes provide source and return paths for the at least one electrical signal to/from the active electrode 202 and the return electrode (which is either located on active electrode 202 or elsewhere as discussed above). The control unit 224 may control the electrical impulse generator 220 for generation of the signal suitable for amelioration of the ailment when the signal is applied to the electrode 202. It is noted that source 204 may be referred to by its function as a pulse generator.

A suitable electrical voltage/current profile for the stimulating, blocking and/or modulating impulse to the portion or portions of one or more nerves and/or muscles may be achieved using the pulse generator 220. In a preferred embodiment, the pulse generator 220 may be implemented using the power source 222 and control unit 224 having, for instance, a processor, a clock, a memory, etc., to produce a pulse train to the electrode(s) that deliver the blocking and/or modulating fields to the nerve resulting from the electrical impulses.

The parameters of the modulation signal are preferably programmable, such as the frequency, amplitude, duty cycle, pulse width, pulse shape, etc. The impulse signal preferably has a frequency, an amplitude, a duty cycle, a pulse width, a pulse shape, etc. selected to influence the therapeutic result, such as stimulating, blocking and/or modulating some or all of one or more nerve transmissions. For example, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. For example, for treating acute and chronic hypotension (discussed below), the electrical signal may be of a frequency between about 15 Hz to 50 Hz. The electrical signal may have a pulsed on-time of between about 50 to 1000 microseconds, such as between about 100 to 400 microseconds and an amplitude of about 1-20 volts, preferably less than about 12 volts and more preferably between about 2-12 volts. The electrical signal may include one or more of a full or partial sinusoid, a square wave, a rectangular wave, and triangle wave.

Although the specific implementation of the signal source is not of criticality to the invention, by way of example, the source may be purchased commercially, such as a Model 7432 available from Medtronic, Inc. Alternatively, U.S. Patent Application Publications 2005/0075701 and 2005/0075702, both to Shafer, both of which are incorporated herein by reference, contain descriptions of pulse generators that may be applicable for implementing the signal source of the present invention.

An alternative implementation for the signal source of the present invention may be obtained from the disclosure of U.S. Patent Publication No.: 2005/0216062, the entire disclosure of which is incorporated herein by reference. U.S. Patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

With reference to FIGS. 2A, 2B, an exemplary electrode device 100 for delivering an electromagnetic field to a patient will now be described. Electrode device 100 is designed to be introduced into the esophagus of the patient and located therein at a position that (when activated) achieves a therapeutic result. The electrode device 100 includes an inflatable balloon 102 and a catheter, or nasogastral (NG) tube 104, sized and shaped (when the balloon 102 is deflated) to slide into the patient's esophagus.

The balloon 102 has at least one section formed from an electrically-permeable material, preferably a hydrophilic or ion-permeable material. By way of example, balloon 102 may be substantially formed from an ion-permeable, soft, flexible, and/or distensible material with a thickness of about 0.001 inches. Suitable balloon materials for use in the present invention include Pebax®, aromatic polyether polyurethane grades, such as Dureflex® from, for example, Deerfield Urethane in Whately, Mass., thermally conductive polymers or thermoplastic elastomers (TPE) such as those found at Cool Polymers, Inc. in Warwick, R.I. and the like. However, it will be recognized by those skilled in the art that a variety of commercially available balloon materials may be used to carry out the present invention.

The balloon preferably has a length of between about 1-3 cm (such as 2 cm), a diameter of between about 1.5-4.0 cm (such as 2-3 cm), and a fluid pressure therein of between about 1-10 pounds per square inch (such as 2 psi) when inflated. Obviously, under the stresses experienced during insertion, extraction and inflation, the balloon 102 should not separate from the NG tube 104, tear or leak. The NG tube 104 may be of a standard type formed out of polyurethane, measuring about 36 cm long, and having inside and outside diameters of 1.6 mm and 2.5 mm, respectively (although other lengths, diameters, and materials may be employed). In order to assist in the placement of the balloon 102 at a desired location within the esophagus, the NG tube 104 may include markers along its length, such as one marker about every 1 cm.

With reference to FIG. 2B, the NG tube 104 includes an internal passageway 106 and an external surface 108. At least one electrode 110 is coupled to the external surface 108 of the NG tube 104 (such as by a UV curable adhesive, such as Dymax 204-CTH). By way of example, the at least one electrode 110 may be of a general cylindrical shape and may extend around the external surface 108 of the NG tube 104. Although there are a number of sizes and shapes that would suffice to implement the electrode 110, by way of example, the at least one electrode 110 may be between about 1.0-1.5 mm long (such as 1.27 mm), may have an outside diameter of between about 2.6-2.85 mm (such as 2.77 mm), and may have an inside diameter of between about 2.5-2.75 mm (such as 2.67 mm). A suitable electrode 110 may be formed from Pt-IR (90%/10%), although other materials or combinations or materials may be used, such as platinum, tungsten, gold, copper, palladium, silver or the like.

Those skilled in the art will also recognize that a variety of different shapes and sizes of electrodes may be used. By way of example only, electrode shapes according to the present invention can include ball shapes, twizzle shapes, spring shapes, twisted metal shapes, annular, solid tube shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like.

In addition, those skilled in the art will recognize that the presence of balloon 102 and the conductive fluid changes the electrical characteristics of the electrode. Specifically, this configuration creates a larger "electrode" having a substantially spherical shape with a diameter of about 2-3 cm (depending on the diameter of balloon 102).

A conductor 112 extends through the internal passageway 106 of the NG tube 104 and electrically connects to the electrode 110. By way of example, the conductor 112 may be a solid silver wire of about 0.25 mm diameter insulated with a PTFE material of about 0.33 mm diameter. The diameter of the insulating material of the conductor 112 should be less than the internal diameter of the NG tube 104 such that fluid may freely flow therein despite the presence of the conductor 112. The conductor 112 may be laser welded to the electrode 110 using known procedures.

A fluid, preferably a saline solution, passes into the balloon 102 through the NG tube 104 to inflate same. The balloon 102 is sized, shaped and located about the electrode 110 and a portion of the NG tube 104 such that when the balloon is inflated with fluid, the electrode 110 is substantially centrally located within an interior volume of the balloon 102. This configuration has several advantages over conventional electrode configurations, such as: (i) the metal of the electrode 110 is not too close to, and never comes in contact with, the patient's tissue, which means that there is no concern about tissue necrosis or excessive electric fields in the tissue; (ii) the electrode 110 may be used with direct current signal sources since any Faradic Products (e.g. OH$^-$, H$_2$O$_2$) would not reach excessively high concentrations at the tissue site; (iii) as the balloon 102 is filled with saline, the surface of the balloon 102 wets and permits good contact with the surrounding tissue of the patient, which may otherwise be dry; and (iv) the material of the balloon 102 is preferably very soft and flexible such that it gently conforms to the surrounding tissue of the esophagus.

To inflate the balloon 102, a number of features are provided with the device 100. A pilot balloon assembly 130, which may be of a standard type, is located at a proximal end of the device 100. The pilot balloon assembly 130 is in fluid communication with the NG tube 104 via fluid tube 132. The fluid tube 132 may enter the NG tube 104 along with the conductor 112, and the entry point may be sealed with an adhesive, such as Dymax 204-CTH UV curable adhesive. The pilot balloon assembly 130 includes a spring loaded valve that opens when introducing fluid into the pilot and the fluid tube 132, and/or when removing fluid therefrom.

The NG tube 104 may include a first aperture 114 through which the conductor 112 passes from the internal passageway 106 to the at least one electrode 110. The NG tube 104 may include second and third apertures 116, 118 extending from the internal passageway 106 to the external surface 108, and through which fluid may pass to inflate and deflate the balloon 102 (as will be discussed in more detail later herein). Preferably, the second and third apertures 116, 118 are disposed at proximal and distal ends 120, 122 of the balloon 102, respectively, and the first aperture 114 is located between the second and third apertures 116, 118.

The inflation process preferably includes a priming phase followed by an inflation phase. The priming phase preferably takes place prior to introducing the device 100 into the patient's esophagus. In the priming phase, a source of fluid, such as saline, is coupled to the pilot balloon assembly 130. The source of fluid may be a fluid filled syringe or the like. With the balloon 102 in a generally vertical orientation (with distal end 120 up), fluid is preferably introduced into the pilot, the fluid tube 132, the NG tube 104 and the balloon 102 via the syringe. The fluid will enter the balloon 102 mostly via the second and third apertures 116, 118. Air will tend to collect at the distal end 120 of the balloon 102 as the fluid enters the device and urges the air in that direction. Again, keeping the balloon upright, at least some of the fluid is drawn out of the balloon 102 by reversing the fluid flow at the pilot balloon assembly 130 and source of fluid. This reversal of fluid flow will create a vacuum and draw all the air out of the balloon 102 via the second aperture 116. Of course, there may be other ways to prime the device 100, however, the above approach is believed to be suitable.

After the device 100 is inserted into the patient's esophagus (preferably through the nasal passage), the inflation phase begins. The inflation phase includes causing the fluid to flow into the device 100 from the source (e.g., the syringe) until a desired balloon size and/or pressure is reached, such as the aforementioned 1-3 cm length, 1.5-4.0 cm diameter, and/or 1-10 psi pressure.

The electrical properties of the electrode 110, the fluid, and the material of the balloon 102 are preferably designed such that a resistance therethrough is no more than about 1000 Ohms, preferably no more than 500 Ohms and more preferably 200 Ohms or less. In an exemplary embodiment, the impedance through the electrode 110, the fluid, and the material of the balloon 102 should be no more than about 200 Ohms at 1000 Hz. The electrical properties of the fluid may be as important as those of the electrode 110 in this regard. The electrically conducting fluid should have a threshold conductivity to provide a suitable conductive path between electrode 110 and the outer wall of the balloon 102. The electrical conductivity of the fluid (in units of milliSiemans per centimeter or mS/cm) will typically be between about 1 mS/cm and 200 mS/cm and will usually be greater than 10 mS/cm, preferably will be greater than 20 mS/cm and more preferably greater than 50 mS/cm. In one embodiment, the electrically conductive fluid is isotonic saline, which has a conductivity of about 17 mS/cm. Applicant has found that a more conductive fluid, or one with a higher ionic concentration, will usually provide optimal results. For example, a saline solution with higher levels of sodium chloride than conventional saline (which is on the order of about 0.9% sodium chloride) e.g., on the order of greater than 1% or between about 3% and 20%, may be desirable. A fluid of about 5% saline (e.g., approximately 100 mS/cm) is believed to work well, although modifications to the concentration and the chemical make-up of the fluid may be determined through simple experimentation by skilled artisans.

As noted above, the material of the balloon 102 is preferably slightly water-permeable or hydrophilic so that when the balloon 102 is filled with saline, the surface of the balloon 102 wets. Preferably, when filled with 10 cc of saline, the flux of saline out of the balloon 102 (into a similar saline solution) should not exceed about 1 cc per hour. Lubrizol Tecophilic HP93A-100 is a material with these properties.

In an alternative embodiment, the electrode 110 may be implemented via the fluid itself within the balloon 102. Although a 5% saline solution would have a relatively high resistance compared to a metal electrode 110 implementation, those skilled in the art would appreciate that higher conductivity fluid solutions may be employed for such purposes or a larger diameter and/or shorter tube may be utilized to increase the conductivity. Additionally or alternatively, the conductor 112 may be implemented using the conductive fluid used to fill the balloon 102; indeed, such fluid is within the passage 106 anyway. Again, relatively high conductivity fluid would be desirable.

Figure 3:
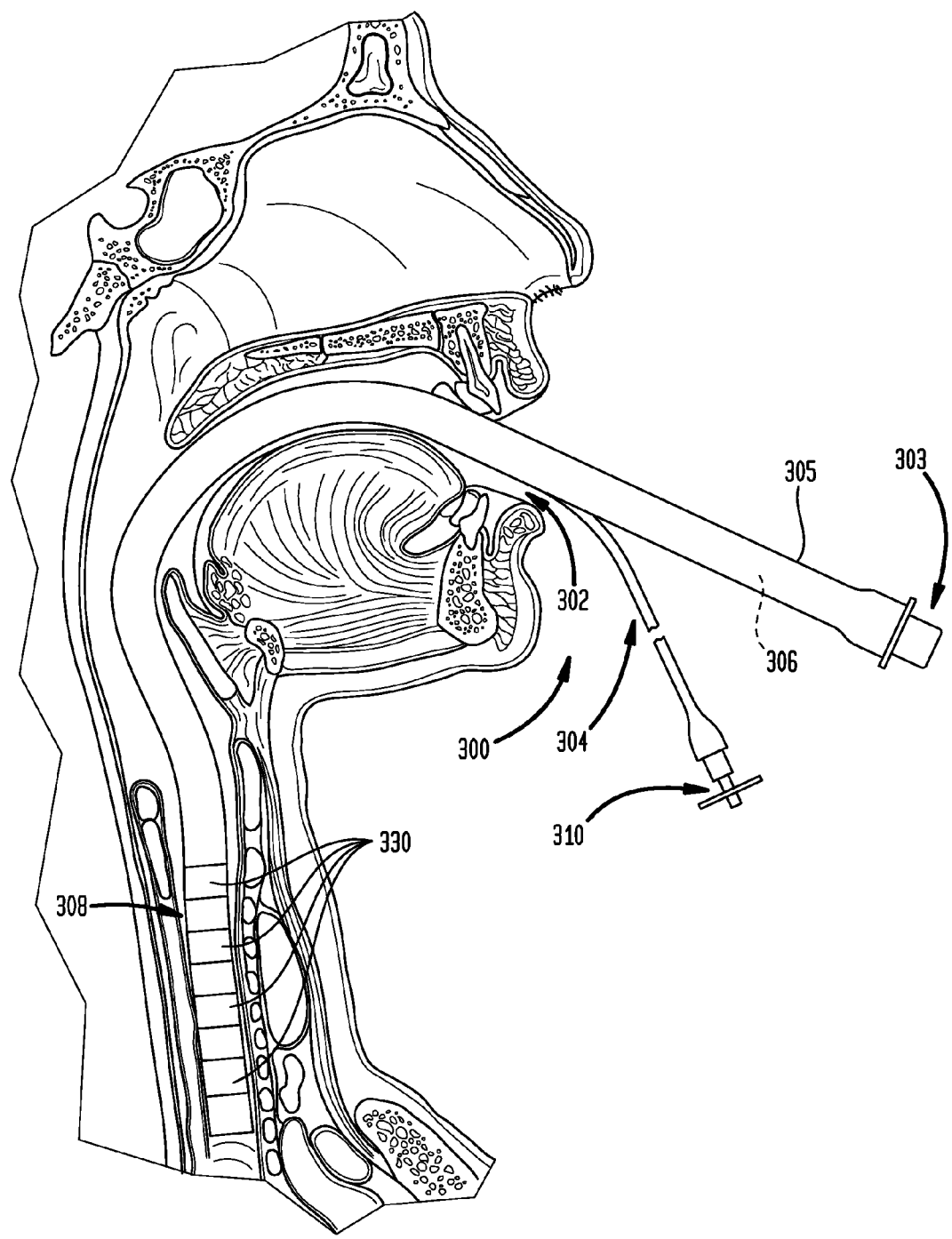
FIG. 3 illustrates another alternative embodiment of the present invention for use in a patient's trachea.

Referring now to FIG. 3, an alternative embodiment for the treatment of hypotension includes a device 300 introduced through the trachea 302 of a patient. As shown, device 300 includes an endotracheal tube 303 that is inserted into the patient under intubation as is well known in the art. Tube 303 comprises a flexible shaft 305 with an inner lumen 306, and a distal electrode assembly 308. Note that electrode assembly 308 may be an integral part of tube 303 or it may be a separate device that is inserted through the inner lumen 306 of a standard endotracheal tube. Many types of conventional endotracheal tubes may be used, such as oral un-cuffed, oral cuffed, Rae tube, nasal tube, reinforced tube, double-lumen tubes and the like.

In the preferred embodiment, electrode assembly 308 comprises a series of annular electrodes 330 (preferably between about 2 to 8) positioned on the exterior surface of endotracheal tube 303. Electrodes 330 preferably have a length of about 0.05-2 cm and are preferably spaced from each other by a distance of between about 1 to 2 cm center to center. In certain embodiments, electrodes 330 have alternating polarities such that the current is passed between two of the electrodes 330 and the electrical circuit is completed at the target site. In other embodiments, electrodes 330 all have the same polarity and a return electrode (not shown) consisting of an EKG-like electrode with a sticky, conductive surface is placed at any convenient location on the exterior of the patient's body.

In use, an electrical stimulation signal is applied to one or more electrodes of electrode assembly 308 such that electrical impulses travel from the electrode(s) through the tracheal tissue to the target site. In the preferred embodiment for treating hypotension, the target site is one or more nerves located adjacent to or near the cricoid cartilage. The endotracheal tube is introduced through the trachea such that the electrodes 330 are positioned at about the middle of the larynx and extend caudally. Applicant has discovered a unique electrical signal that will increase blood pressure to treat acute or chronic hypotension when applied from the lumen of the patient's trachea around the cricoid cartilage.

In an alternative embodiment, electrode assembly 308 may comprise a balloon electrode device (not shown) that includes an electrode positioned within the interior of a balloon as described above in FIGS. 2A and 2B. In this embodiment, tube 303 may include a fluid passage 304 fluidly coupling the inner lumen 306 with a source of electrically conductive fluid (not shown) and a proximal port 310 for coupling to a source of electrical energy (also not shown). Tube 303 may also include an aspiration lumen (not shown) for aspirating the conductive fluid and/or other bodily fluids as is well known in the art. The interior of the balloon is fluidly coupled to the fluid passage 304 for delivery of electrically conductive fluid into the balloon. The balloon is sized and shaped such that, when inflated with the conductive fluid, it will contact, or come in close proximity with, the inner walls of the patient's trachea 302.

Experimental Data

Experiments were performed to identify exemplary methods of how electrical signals can be supplied to the peripheral nerve fibers that innervate and/or control the myocardium (and/or vasoconstriction) to (i) reduce the sensitivity of the muscle to the signals of tonic contraction, (ii) to blunt the intensity of, or break the tonic over-contraction once it has been initiated, and/or (iii) to constrict the vessels to increase blood pressure. In particular, specific signals, selected from within a range of known nerve signals, were applied to the vagus nerves and/or the sympathetic nerves in guinea pigs, to produce selective interruption or reduction in the effects of vagal nerve activity leading to attenuation of histamine-induced hypotension and bronchoconstriction.

Experimental Procedure 1

Male guinea pigs (400 g) were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Both vagus nerves were exposed in the neck and connected to electrodes to allow selective stimuli of these nerves. Following 15 minutes of stabilization baseline hemodynamic and airway pressure measurements were made before and after the administration of repetitive doses of i.v. histamine.

Following the establishment of a consistent response to i.v. histamine, vagal nerve stimulation was attempted at variations of frequency, voltage and pulse duration to identify parameters that attenuate responses to i.v. histamine. Hypotension and bronchoconstriction in response to i.v. histamine are known to be due both to direct muscle effects and to stimulation of vagal nerves to release acetylcholine.

At the end of vagal nerve challenges, atropine was administered i.v. before a subsequent dose of histamine to determine what percentage of the histamine-induced hypotension and bronchoconstriction was vagal nerve induced. This was considered a 100% response. Success of electrical interruption in vagal nerve activity in attenuating histamine-induced hypotension and bronchoconstriction was compared to this maximum effect. Euthanasia was accomplished with intravenous potassium chloride.

The blood pressure and heart rate were measured to track the subjects' vital signs. In order to measure the bronchoconstriction, the airway pressure was measured with two sensors. In all of the following graphs, the top line BP (red) shows blood pressure, the second line AP1 (green) shows airway pressure, the third line AP2 (blue) shows airway pressure on another sensor and the last line HR is the heart rate derived from the pulses in the blood pressure.

Figure 4:
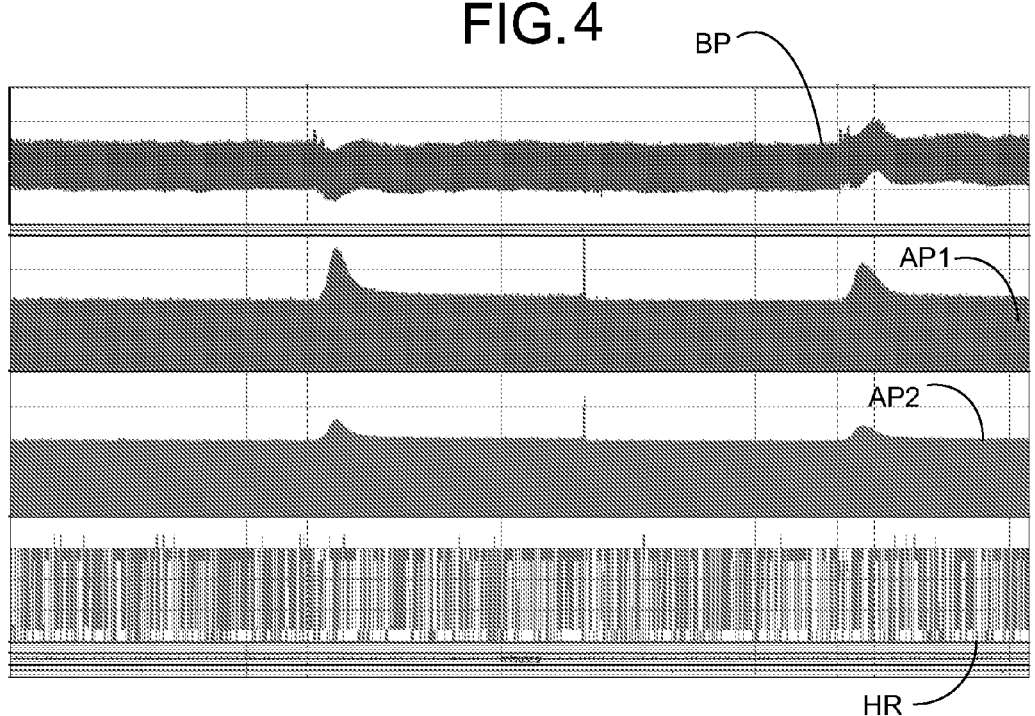
FIGS. 4-12 graphically illustrate exemplary experimental data obtained in accordance with multiple embodiments of the present invention.

FIG. 4 graphically illustrates exemplary experimental data on guinea pig #5. The graphs of FIG. 4 show the effect of a 25 Hz, 400 µS, 1V square wave signal applied to both left and right vagus nerve in guinea pig #5 when injected with 8 µg/kg histamine to decrease blood pressure and increase airway pressure. The first trough and peak, respectively, in blood and airway pressures are from histamine alone, the next peak and peak, respectively, are histamine and signal applied. The blood pressure is clearly increased, but the heart rate is not affected, by the 25 Hz, 400 µS, 1V square-wave signal on the vagus nerve. It also is clearly shown that the increase in airway pressure due to histamine is reduced in the presence of the 25 Hz, 400 µS, 1V square wave on the vagus nerve.

Figure 5:
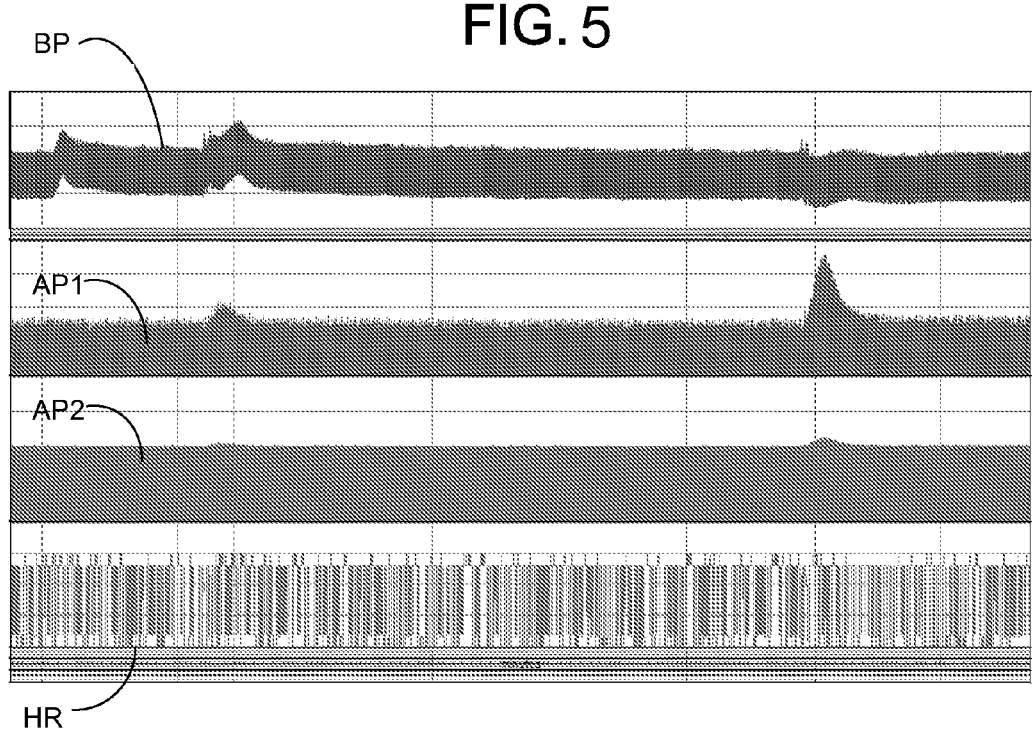

FIG. 5 graphically illustrates additional exemplary experimental data on guinea pig #5. The graphs of FIG. 5 show the effect of a 25 Hz, 200 µS, 1V square wave signal applied to both the left and right vagus nerves in guinea pig #5 when injected with 8 µg/kg histamine. The first blood pressure peak, without an effect on airway pressure, is signal alone. The second peak and peak, respectively, are from histamine and signal applied simultaneously, whereas the third trough and peak, respectively, are from histamine alone. The blood pressure clearly is increased by the 25 Hz, 200 µS, 1V square wave signal, without simply driving the heart rate higher. It also is shown clearly that the increase in airway pressure due to histamine is reduced in the presence of the 25 Hz, 200 µS, 1V square wave on the vagus nerve. It is clear that the blood pressure increase and airway pressure reduction are even better with the 200 µS pulse width than the 400 µS signal.

Figure 6:
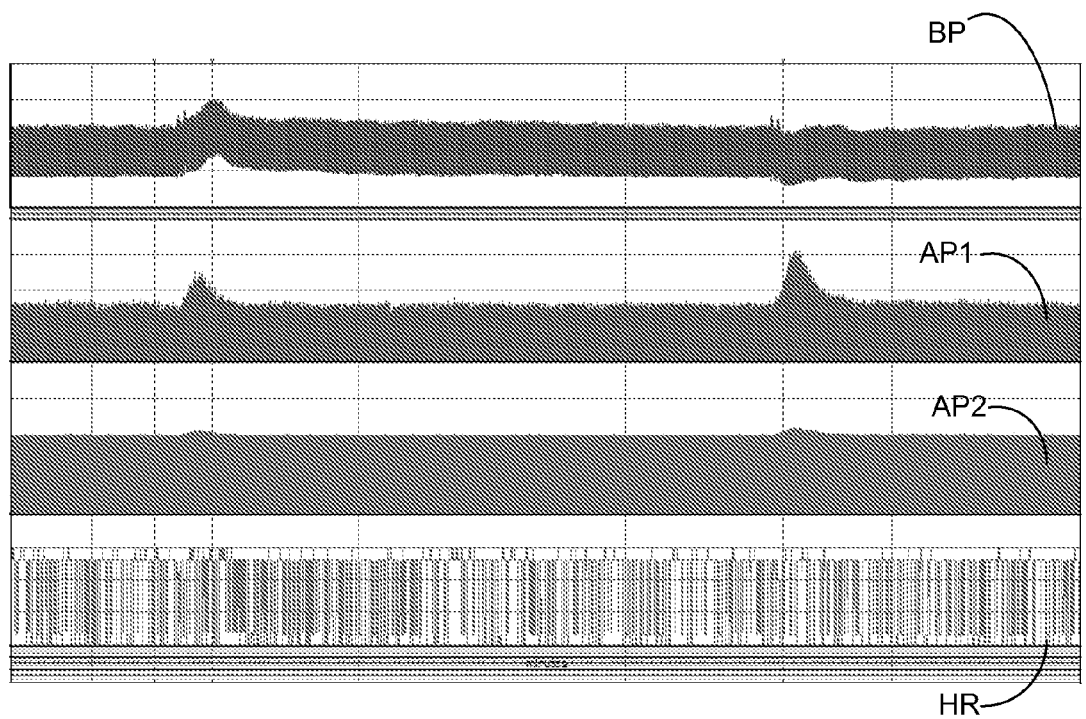

FIG. 6 graphically illustrates further exemplary experimental data on guinea pig #5. The graphs of FIG. 6 show repeatability of the effect seen in the previous graph. The animal, histamine and signal are the same as the graphs in FIG. 5.

It is significant that the effects shown above were repeated several times with this animal (guinea pig #5), without any loss of nerve activity observed. We could move the electrodes proximally and distally along the vagus nerve and achieve the same effect. It was, therefore, concluded that the effect was being achieved by means other than simply damaging the nerve.

Figure 7:
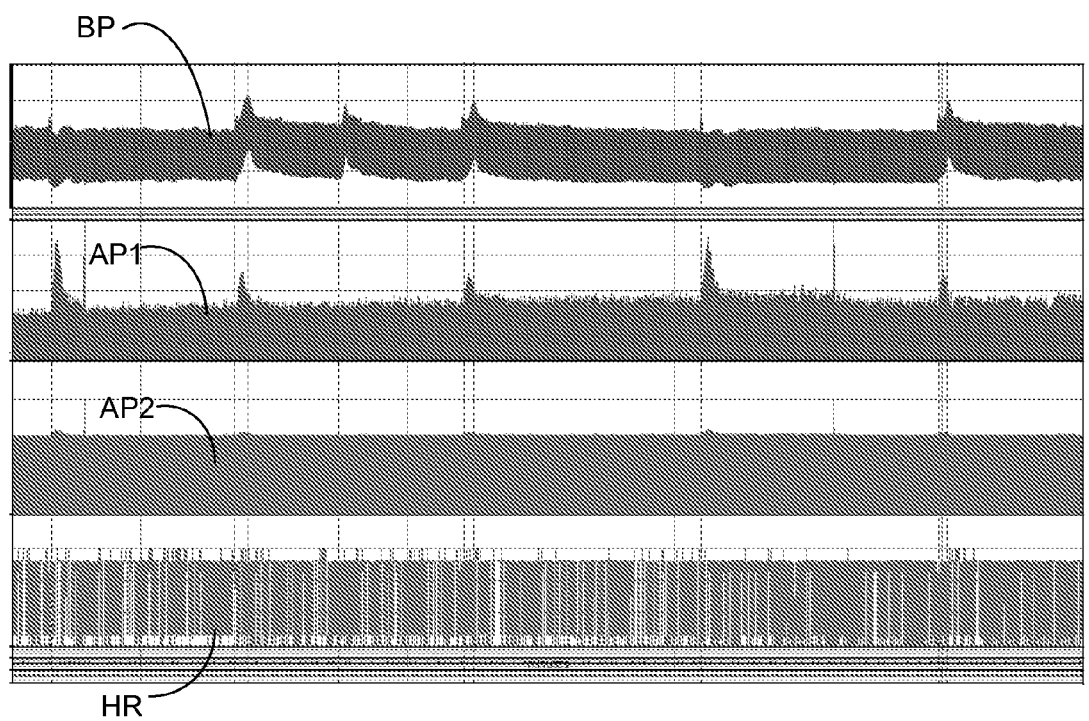

FIG. 7 graphically illustrates subsequent exemplary experimental data on guinea pig #5. The graphs of FIG. 7 show the effect of a 25 Hz, 100 µS, 1V square wave that switches polarity from + to − voltage every second. This signal is applied to both left and right vagus nerve in guinea pig #5 when injected with 8 µg/kg histamine. From left to right, the vertical dotted lines coincide with blood pressure/airway events associated with: (1) histamine alone (blood pressure trough with a large airway spike—followed by a very brief manual occlusion of the airway tube); (2) histamine with a 200 µS signal applied (blood pressure peak with a smaller airway spike); (3) a 100 µS electrical signal alone (blood pressure peak with no airway spike); (4) histamine with a 100 µS signal applied (blood pressure peak with a smaller airway spike again); (5) histamine alone (blood pressure trough with a large airway spike); and (6) histamine with the 100 µS signal applied (blood pressure peak with a smaller airway spike again).

The animal's blood pressure is substantially increased by this signal, but as with the prior animal (guinea pig #4), the heart rate is not affected. The blood and airway pressure effects appear to be better with the 100 µS pulse width than the 200 µS pulse width signal. This evidence strongly suggests that the decrease in blood pressure due to histamine can be effectively negated and overcome by the application of a 25 Hz, 100 µS, 1V square wave with alternating polarity on the vagus nerve. This evidence also strongly suggests that the respective increase in airway pressure can be significantly reduced by the application of a 25 Hz, 100 µS, 1V square wave with alternating polarity on the vagus nerve.

Figure 8:
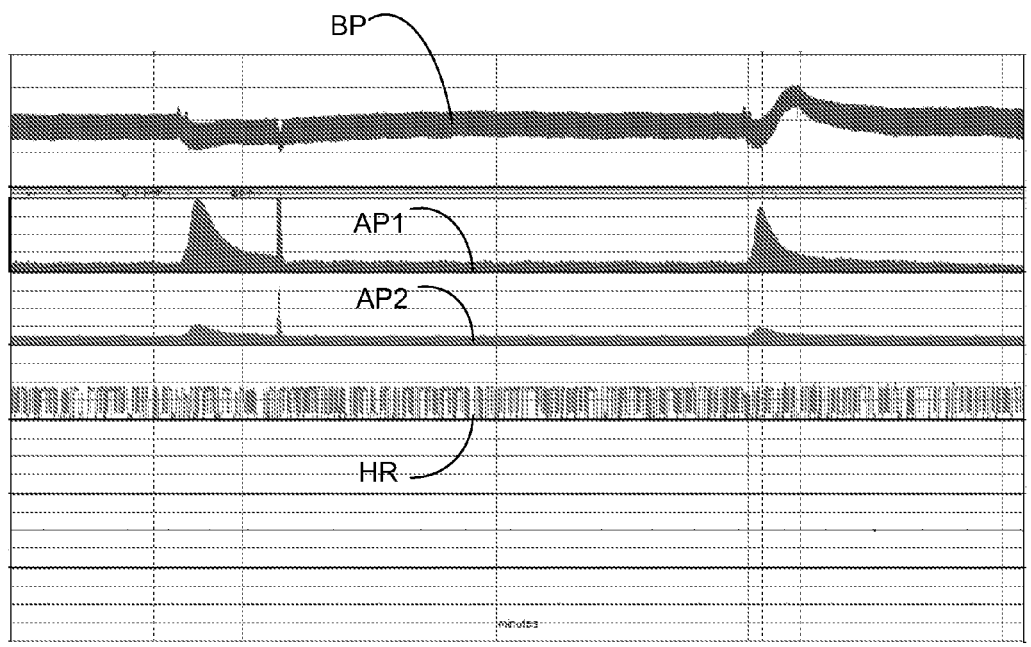

FIG. 8 graphically illustrates exemplary experimental data on guinea pig #6. The graphs in FIG. 8 show the effect of a 25 Hz, 200 µS, 1V square wave that switches polarity from + to − voltage every second. This signal is applied to both left and right vagus nerve in guinea pig #6 when injected with 16 µg/kg histamine. Note that this animal demonstrated a very high tolerance to the effects of histamine, and therefore was not an ideal test subject for the histamine-induced effects. However, the animal did provide us with the opportunity to test the signal-only effects on blood pressure and modification of signal parameters.

In this case, the first trough in blood pressure and peak in airway pressure are from histamine alone, followed by a trough-peak pair corresponding to a brief manual occlusion of the airway. The next and final trough-then-peak of the blood pressure, accompanied by a peak in the airway pressure, is histamine with the signal applied. It is clearly shown that the blood pressure is increased by application of a 25 Hz, 200 µS, 1V square-wave signal with alternating polarity on the vagus nerve, but again, the heart rate is not affected. Furthermore, the increase in airway pressure due to histamine is reduced moderately in its peak, and most definitely in its duration, when in the presence of the 25 Hz, 200 µS, 1V square wave with alternating polarity on the vagus nerve.

Figure 9:
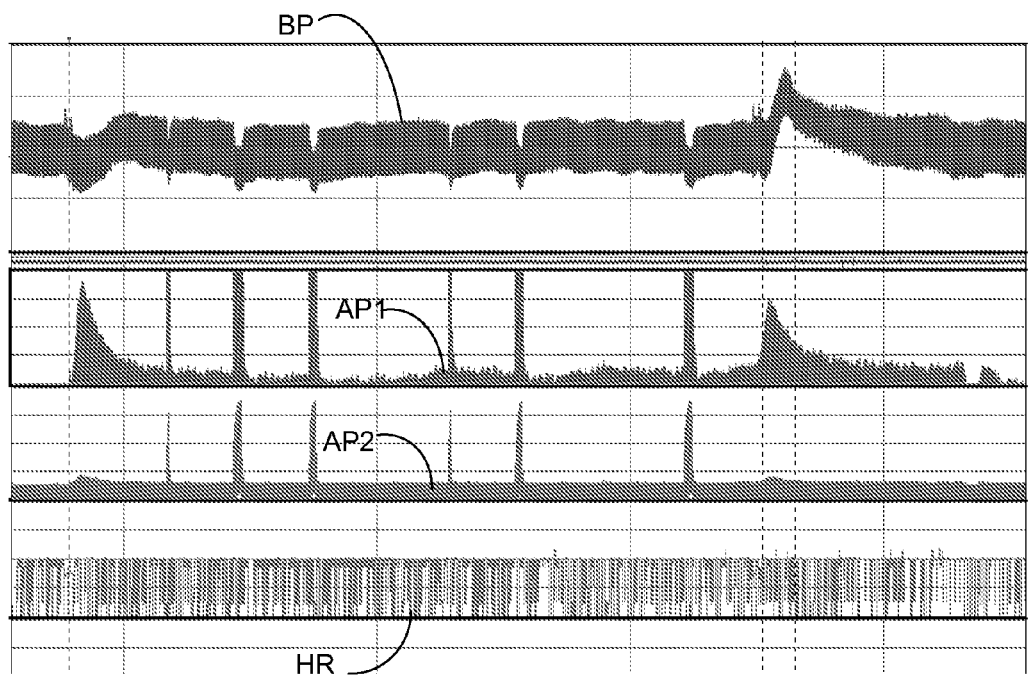

FIG. 9 graphically illustrates additional exemplary experimental data on guinea pig #6. As mentioned above, guinea pig #6 in the graphs of FIG. 8 above needed more histamine than other guinea pigs (16-20 µg/kg vs 8 µg/kg) to achieve the desired increase in airway pressure. Also, the beneficial effects of the 1V signal were less pronounced in pig #6 than in #5. Consequently, we tried increasing the voltage to 1.5V. The first blood pressure trough and airway pressure peak is from histamine alone. A series of six manual occlusions of the airway tube followed, each causing a blood pressure trough and airway pressure spike. The next and final blood pressure trough-then-peak and airway pressure peak are the result of histamine with the 1.5V, 25 Hz, 200 µS alternating polarity signal. The beneficial effects on the blood pressure, as well as the airway pressure, are seen with slightly more impact, but not substantially better than the 1V.

Figure 10:
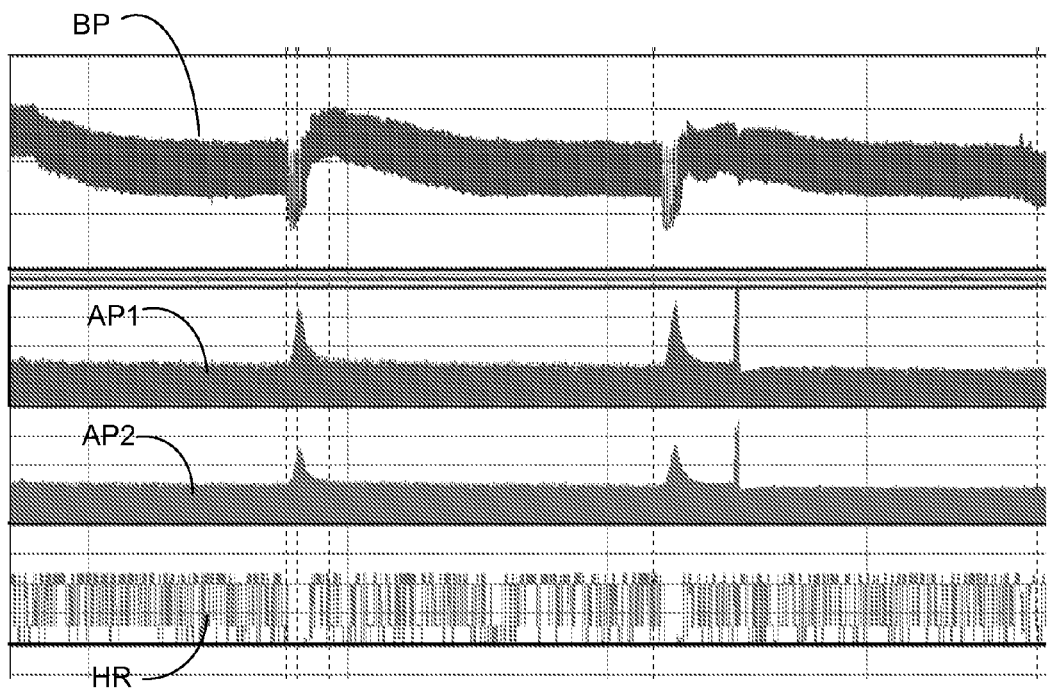

FIG. 10 graphically illustrates further exemplary experimental data on guinea pig #6. Since guinea pig #6 was losing its airway reaction to histamine, we tried to determine if the 25 Hz, 200 µS, 1V, alternating polarity signal could mitigate the effects of a 20V, 20 Hz airway pressure stimulating signal to produce a simulated asthmatic or shock-like response. The first event of a blood pressure trough and an airway pressure peak corresponds to the 20V, 20 Hz stimulator signal applied to simulate shock, then switched over to the 25 Hz, 200 µS, 1V, alternating polarity signal, causing the blood pressure to peak. The second event is the 20V, 20 Hz signal alone, causing a major but rebounding blood pressure trough and an airway pressure peak.

The blood pressure increase after application of the 25 Hz, 200 µS, 1V signal during the first event caused a visible benefit over no signal during the second event. Overall, the effects of the first event look modestly reduced and narrower than those of the second event. The 25 Hz, 200 µS, 1V signal may have some beneficial airway pressure reduction after electrical stimulation of airway constriction. Notably, in both the first and second events, the simulated shock-signal momentarily interfered with the heart rate, until equilibrium could again be reached. After the second event, a brief manual occlusion occurred, spiking the airway pressure and depressing the blood pressure.

On animal #6 we investigated which branch of the vagus nerve had the most effect on the blood pressure. We found that the right branch stimulated with the 25 Hz, 1V, 200 µS signal was responsible for the vast majority of the blood pressure increase. Stimulating the left vagus did not measurably affect the blood pressure.

Figure 11:
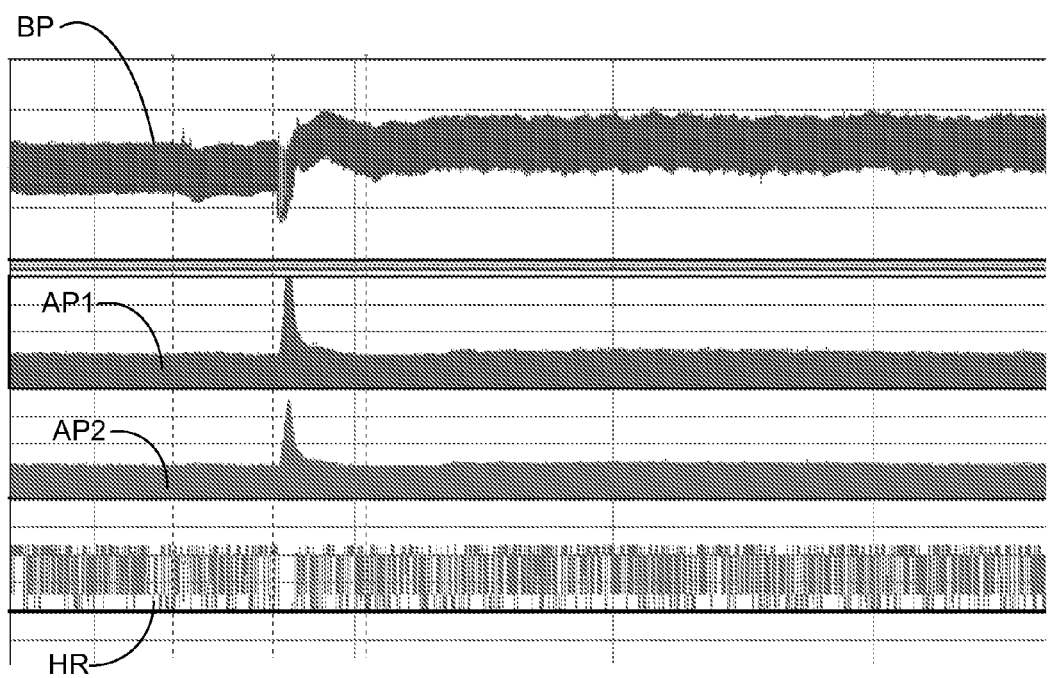

FIG. 11 graphically illustrates subsequent exemplary experimental data. On guinea pig #6 we also investigated the effect of the 1V, 25 Hz, and 200 µS alternating polarity signal on blood pressure. After a brief application of histamine and the asthma/shock-simulating signal, causing a corresponding blood pressure trough and airway pressure peak, the 1V, 25 Hz, and 200 µS alternating polarity signal was applied for 10 minutes. The charts show the sustained increase in blood pressure throughout the 10-minute signal application. Even after application of the signal for 10 minutes continuously, there was no loss of nerve conduction or signs of damage.

In contrast to the previous animals, guinea pig #7 was in distress from the initial preparation before any tests were run. Its blood pressure was low and sinking while the airway pressure was uneven and rising. This animal's blood pressure could be raised with our 25 Hz, 1V, 200 µS signal but without the signal, it kept falling. When the blood pressure was almost gone, we kept our signal on for several minutes and kept the animal alive for that time.

Figure 12:
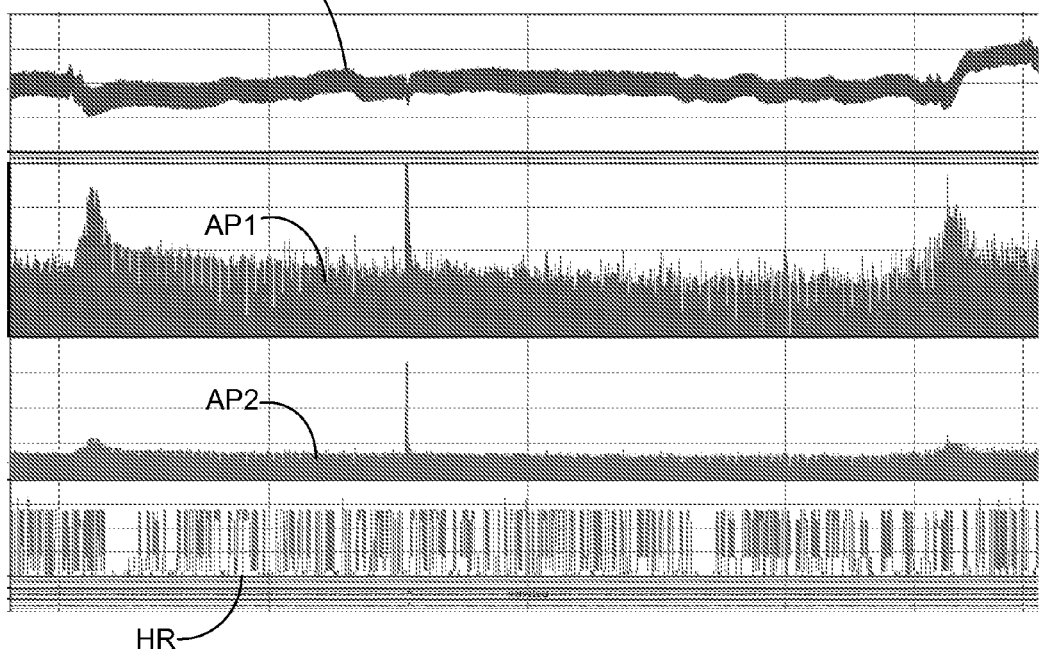

FIG. 12 graphically illustrates exemplary experimental data on guinea pig #8. The graph below shows the effect of a 25 Hz, 200 µS, 1V square wave that switches polarity from + to − voltage every second. This signal is applied to both left and right vagus nerve in guinea pig #8 when injected with 12 µg/kg histamine. The first trough-peak pair in blood and airway pressures is from histamine alone, whereas the next trough-peak pair represents a manual occlusion. The third pair, a blood pressure trough-then-peak and an airway pressure peak, is histamine with the signal applied. The blood pressure is clearly increased by this signal, 25 Hz, 200 µS, 1V square wave with alternating polarity, but the heart rate is not affected. It clearly is shown also that the increase in airway pressure due to histamine is reduced in the presence of the 25 Hz, 200 µS, 1V square wave with alternating polarity on the vagus nerve. We have reproduced this effect multiple times, on 4 different guinea pigs, on 4 different days.

The blood pressure in guinea pigs can be significantly increased by applying appropriate electrical signals to the vagus nerve. Likewise, airway constriction induced by histamine in guinea pigs can be significantly reduced by applying appropriate electrical signals to the vagus nerve.

With a 25 Hz, 1V, 100-200 µS signal applied to the right branch or both branches of vagus nerve, a significant increase in guinea pig blood pressure is observed. This has been repeated on multiple animals many times. There is no evidence of nerve damage. Such a signal may be applied in the treatment of low blood pressure in conditions such as orthostatic hypotension, hypovolemic shock, septic shock and anaphylactic shock.

The 25 Hz, 1V, 100-200 µS signal applied to the vagus nerve also significantly reduced airway constriction due to histamine.

Application of the signal to the vagus nerve appears to have some effects lasting long after the signal is removed. Specific, repeatable experimentation may be done to substantiate these longer lasting effects.

Additional testing on the guinea pig model may quantify the extent to which longer lasting effects remain after stimulation is removed.

Experimental Procedure 2

In U.S. patent application Ser. No. 10/990,938 filed Nov. 17, 2004 (Publication Number US2005/0125044A1), Kevin J. Tracey proposes a method of treating many diseases including, among others, asthma, anaphylactic shock, sepsis and septic shock by electrical stimulation of the vagus nerve. However, the examples in the Tracey application use an electrical signal that is 1 to 5V, 1 Hz and 2 mS to treat endotoxic shock, and no examples are shown that test the proposed method on an asthma model, an anaphylactic shock model, an orthostatic hypotension model, a hypovolemia model or a sepsis model. The applicants of the present application performed additional testing to determine if Tracey's proposed method has any beneficial effect on blood pressure or bronchial constriction. The testing followed the model described above, which demonstrated the efficacy of the method used in accordance with the present application. The applicants of the present application sought to determine whether Tracey's signals can be applied to the vagus nerve in guinea pigs to increase blood pressure and/or attenuate histamine-induced bronchoconstriction.

Male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 1 to 5 volts, 1 Hz, 2 mS to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

The blood pressure and heart rate were measured to track the subjects' vital signs. In order to measure the bronchoconstriction, the airway pressure was measured in two places. In all the following graphs, the top line BP (red) shows blood pressure, second line AP1 (green) shows airway pressure, third line AP2 (blue) shows airway pressure on another sensor, the last line HR is the heart rate derived from the pulses in the blood pressure.

Figure 13:
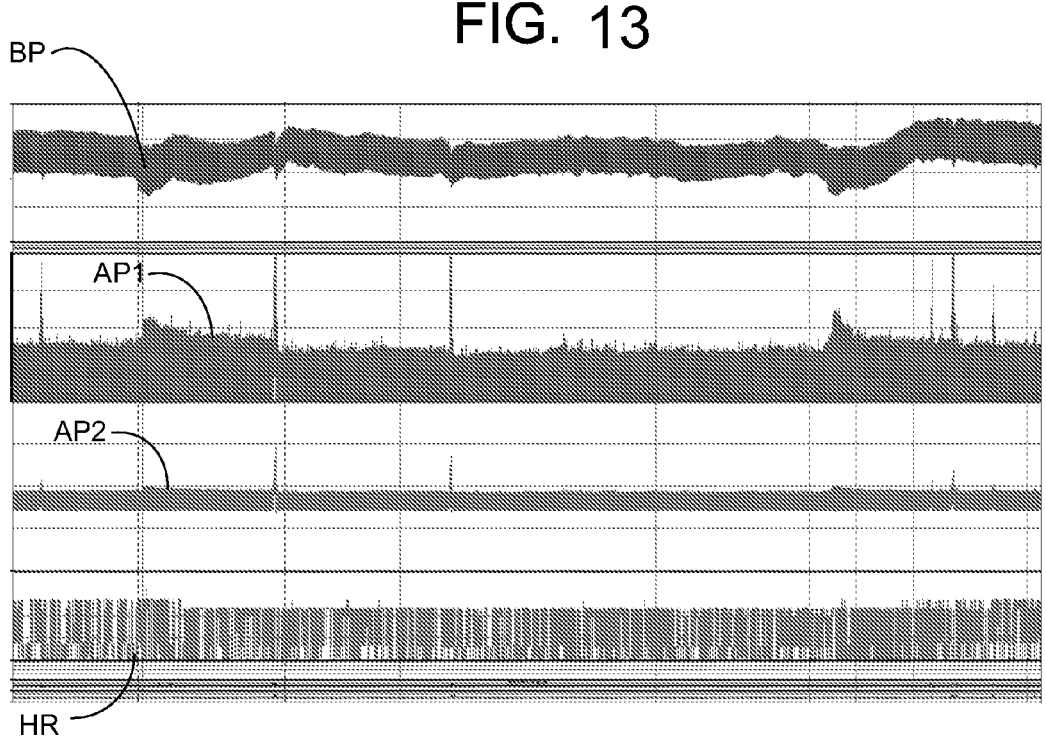
FIGS. 13-18 graphically illustrate the inability of signals taught by U.S. patent application Ser. No. 10/990,938 to achieve the results of the present invention.

FIG. 13 graphically illustrates exemplary experimental data from a first experiment on another guinea pig. The graph shows the effects of Tracey's 1V, 1 Hz, 2 mS waveform applied to both vagus nerves on the guinea pig. The first trough in blood pressure, corresponding to a first peak in airway pressure, is from histamine alone, followed by a brief manual occlusion, after which Tracey's signal was applied for 10 minutes as proposed in Tracey's patent application. As seen from the second histamine-induced blood pressure trough and airway pressure peak, at the right of the graph, the signal has no noticeable effect on blood pressure or airway pressure. The blood pressure actually rose after the signal was turned off.

Figure 14:
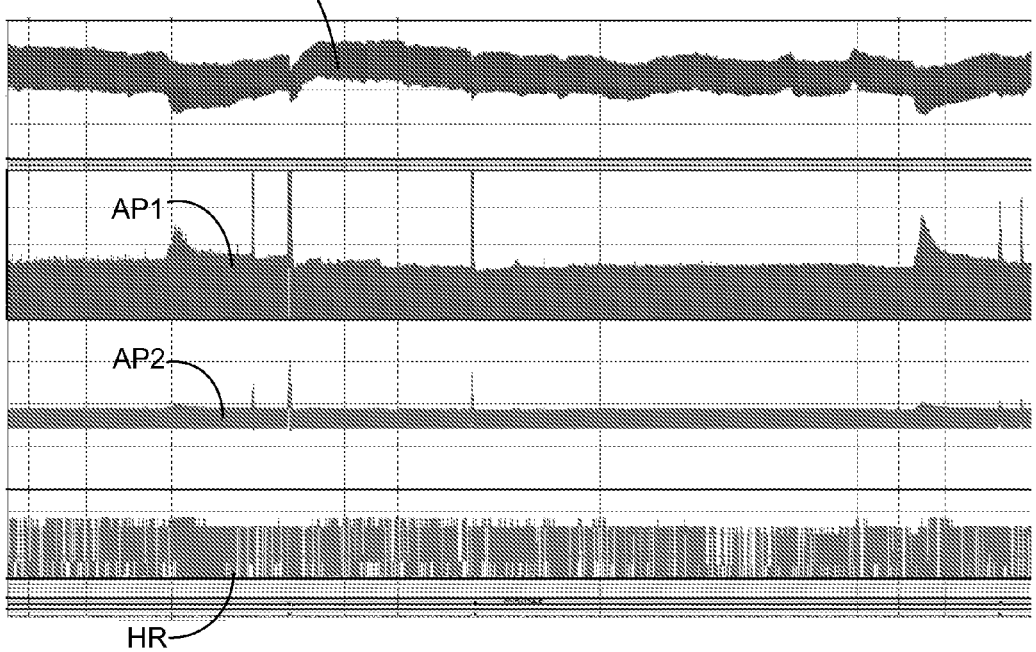

FIG. 14 graphically illustrates exemplary experimental data from a second experiment on the guinea pig in FIG. 13. The graph shows the effects of Tracey's 1V, 1 Hz, 2 mS waveform with the polarity reversed (Tracey did not specify polarity in the patent application) applied to both vagus nerves on the guinea pig. Again, the signal has no beneficial effect on blood or airway pressure. In fact, during application of the signal, the blood pressure was slightly lower, and the signal did not keep the blood pressure from falling when the histamine was applied. Moreover, the second airway peak from the signal and histamine combination is actually higher than the first peak of histamine alone.

Figure 15:
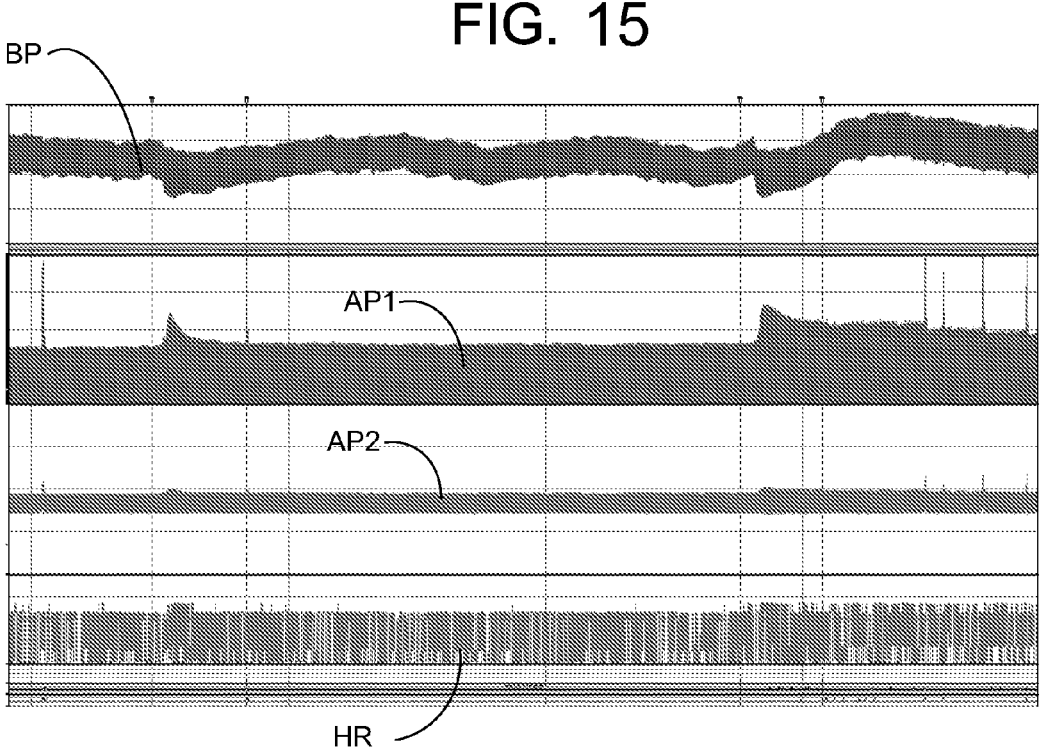

FIG. 15 graphically illustrates exemplary experimental data from a third experiment on the guinea pig in FIG. 13. The graph shows the effects of Tracey's 1V, 1 Hz, 2 mS waveform applied to both vagus nerves on the guinea pig. Again, the signal has no beneficial effect on blood or airway pressure. Analogous to the results in FIG. 14, the signal did not maintain the blood pressure when the histamine was applied. Instead, it increases airway pressure and reduces blood pressure.

Figure 16:
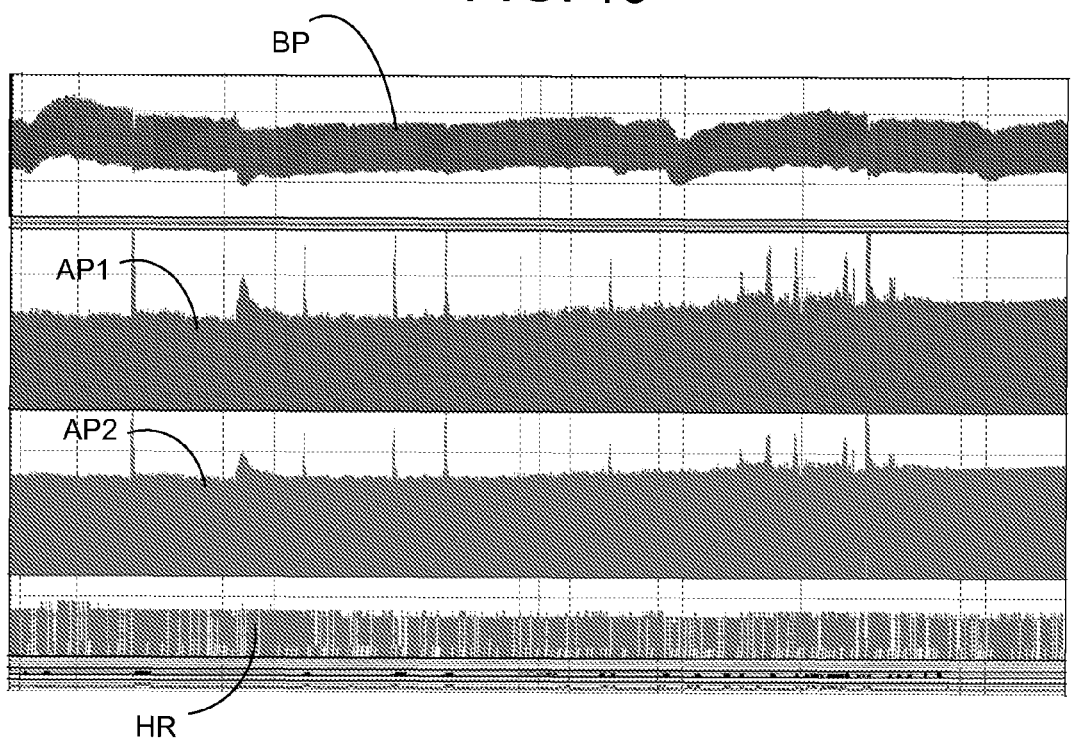

FIG. 16 graphically illustrates additional exemplary experimental data from an experiment on a subsequent guinea pig. The graph shows, from left to right, first a beneficial blood pressure increase from the 1.2V, 25 Hz, 0.2 mS signal disclosed in the present application. The subsequent three electrical stimulation treatments are 1V, 5V, and 2.5V variations of Tracey's proposed signal. It is clear that the Tracey signals do not cause an increase in blood pressure, but rather frequently cause a decrease.

Figure 17:
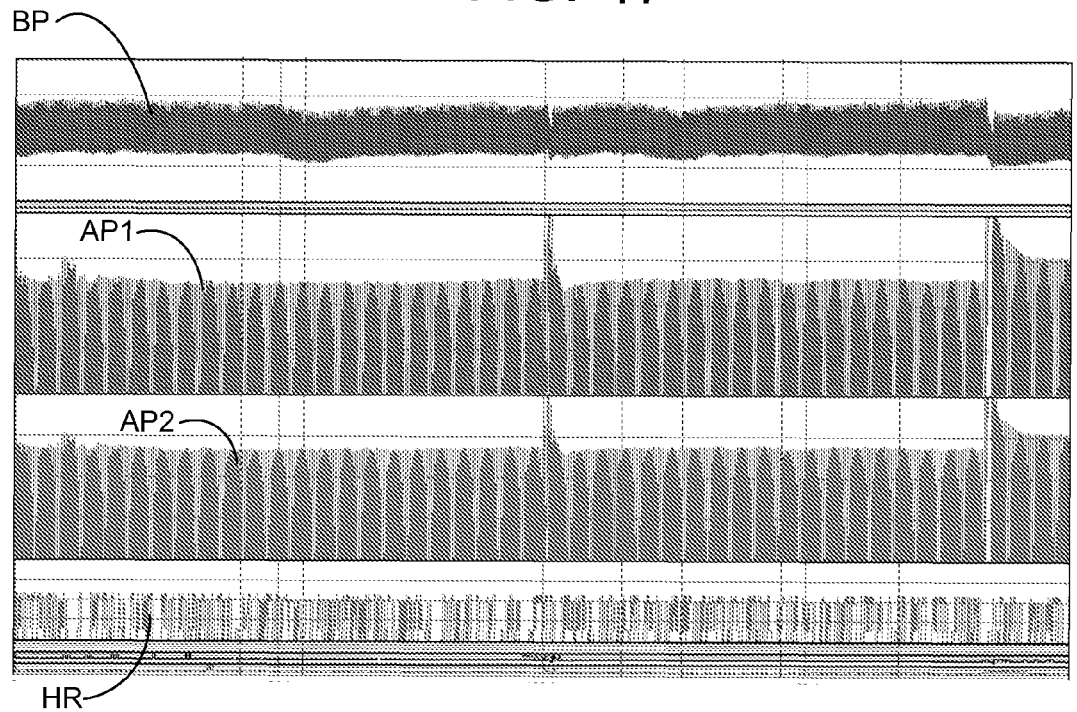

FIG. 17 graphically illustrates further exemplary experimental data from additional experiments using signals within the range of Tracey's proposed examples. None of the signals proposed by Tracey had any beneficial effect on blood pressure. Factoring in a potential range of signals, one experiment used 0.75V, which is below Tracey's proposed range, but there was still no beneficial effect on blood pressure.

Figure 18:
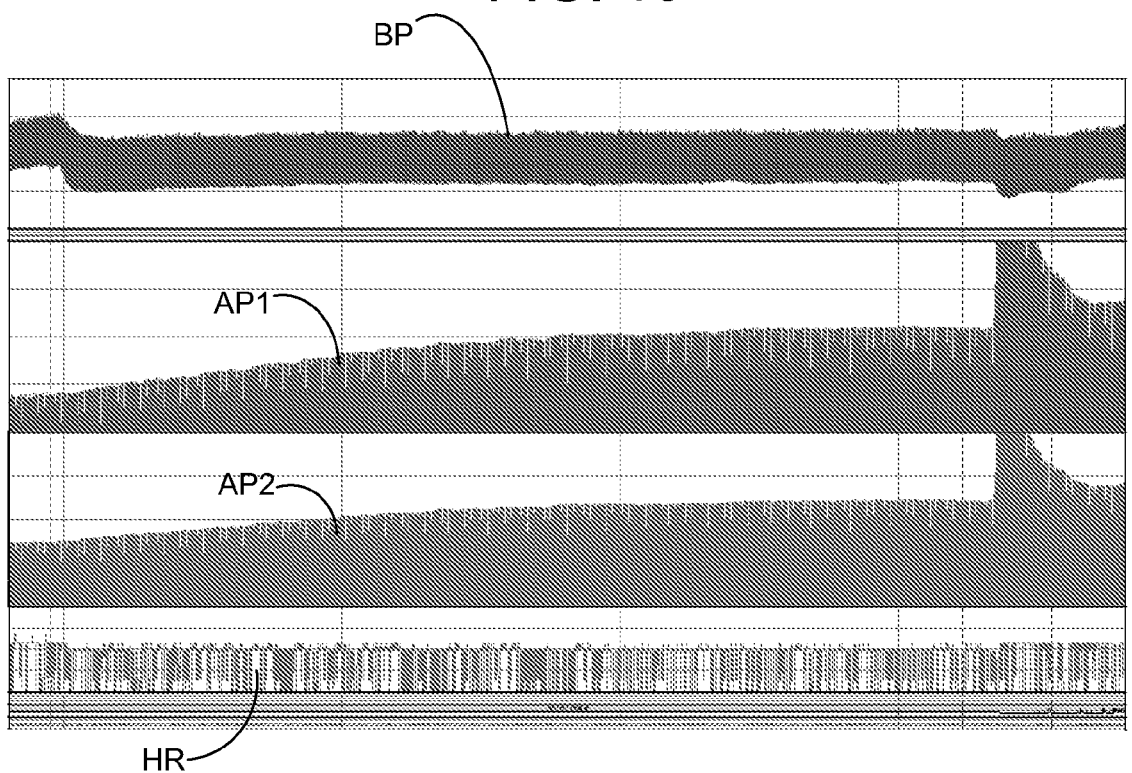

FIG. 18 graphically illustrates exemplary experimental data from subsequent experiments showing the effect of Tracey's 5V, 1 Hz, 2 mS signal on histamine response. The blood pressure fell with application of the Tracey signal and fell even farther with application of the histamine. It is clear that the airway pressure increase is even greater with the signal, and that blood pressure is decreased by the signal.

The full range of the signal proposed by Tracey in his patent application was tested in the animal model of the present application. No reduction in airway pressure was seen. No increase in blood pressure was seen. Most of the voltages resulted in detrimental decreases in blood pressure and detrimental increases in airway pressure.

Experimental Procedure 3

While the above experiments were conducted by inducing hypotension (and/or bronchial constriction) using i.v. histamine, additional test data were obtained in response to anaphylaxis. Fifteen male guinea pigs (400 g) were sensitized by the intraperitoneal injection of ovalbumin (10 mg/kg i.p. every 48 hrs for three doses). Three weeks later animals were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyzed chest wall musculature to remove the contribution of chest wall rigidity from airway pressure measurements. Both vagus nerves were isolated and connected to shielded electrodes to allow selective stimuli of these nerves in the manner disclosed in the one or more embodiments disclosed above. Following fifteen minutes of stabilization, baseline hemodynamic and airway pressure measurements were made before and after the administration of increasing concentrations of ovalbumin (0.001-1.0 mg/kg i.v.). Following the increase in airway pressure and hypotension accompanying the anaphylactic response, vagal nerve modulation was made at variations of frequency, voltage and pulse duration to identity parameters that attenuate the hypotensive and bronchoconstrictive responses. Euthanasia was accomplished with intravenous potassium chloride.

Figure 19:
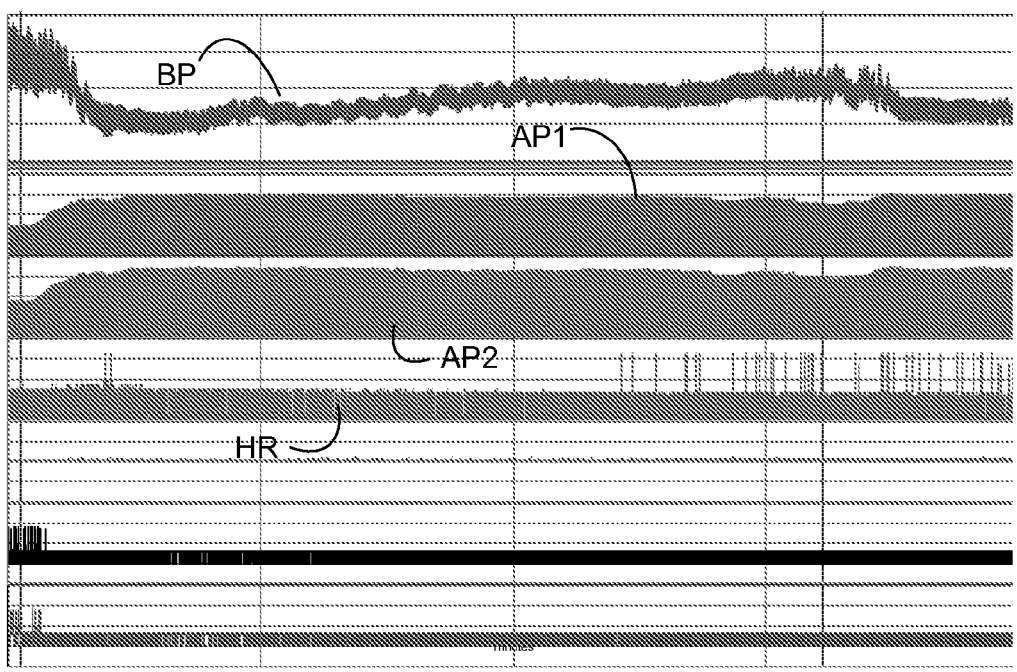
FIGS. 19-21 graphically illustrate exemplary experimental data obtained for the treatment of anaphylaxis according to the present invention.

With reference to FIG. 19, the top line (BP) shows blood pressure, the second line shows airway pressure (AP1), the third line shows airway pressure (AP2) on another sensor, the fourth line is the heart rate (HR) derived from the pulses in the blood pressure. As a baseline of the anaphylactic reaction that is achieved in this model, the first guinea pig's response to the ovalbumin was recorded without any electrical stimulation. The graph in FIG. 19 shows the effect of an injection of 0.75 mg of ovalbumin. About five minutes after the injection, the blood pressure dropped from 125 to 50 mmHg while the airway pressure increased from 11 to 14 cm $H_2O$. This effect was sustained for over sixty (60) minutes with the blood pressure showing some recovery to 90 mmHg.

Figure 20:
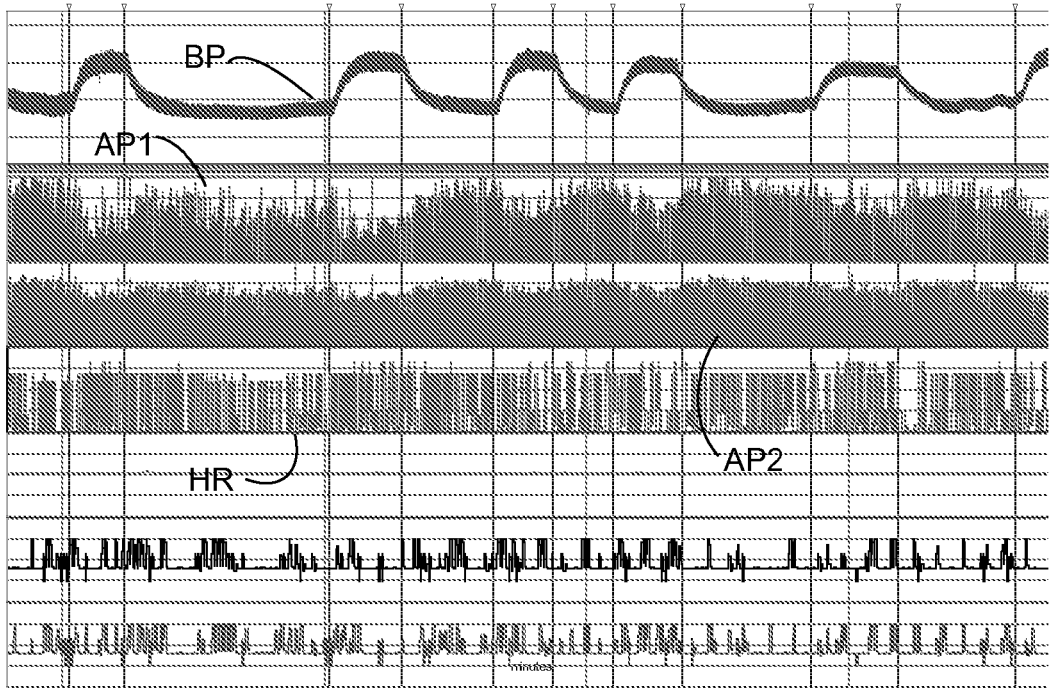

With reference to FIG. 20, another animal (guinea pig #2) was tested to determine the effect of the signals that were shown to be effective in the histamine induced asthma model (Experimental Procedure 1 above). FIG. 20 demonstrates the effect of a 25 Hz, 200 μS, 1.25V square wave signal applied simultaneously to both left and right vagus nerves in sensitized guinea pig #2 after injection with 1.125 mg ovalbumin to cause an anaphylactic response. The larger dose was used to cause a more severe reaction. Starting from the left side of the graph, it may be seen that before electrical stimulation, the blood pressure was severely depressed at 30 mmHg while the airway pressure was almost 22 cm $H_2O$ (9.5 cm increase over baseline). The first peak in blood pressure coincides with the electrical signal applied to the vagus—the blood pressure increased to 60 mmHg (a 100% increase) while the airway pressure reduced by 6.5 cm to about 15.5 cm $H_2O$ (a 68% reduction). The next peak shows the effect repeated. The other peaks show the effects of changing the signal voltage—lowering the voltage results in reduced effectiveness.

Figure 21:
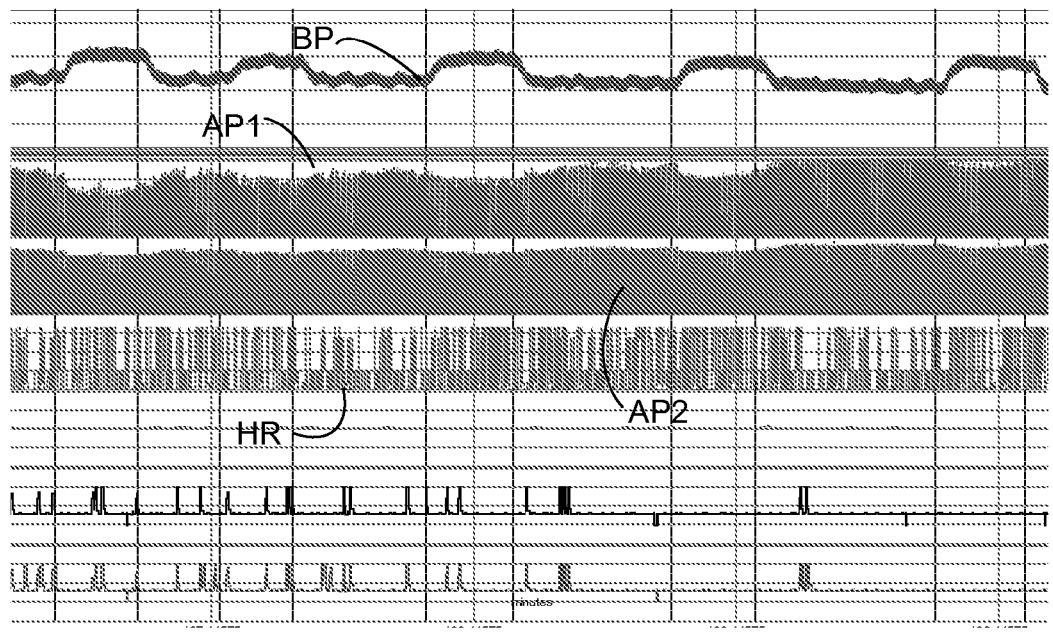

With reference to FIG. 21, the effect of changing the signal frequency and pulse width on blood pressure and airway pressure is shown. The first peak in blood pressure coincides with a 15 Hz, 300 uS, 1.25V electrical signal applied to both sides of the vagus—the blood pressure was increased to 60 mmHg (a 70% increase) while the airway pressure was reduced by 1.5 cm to about 17 cm $H_2O$ (a 25% reduction). The next peak demonstrates a 10 Hz signal—the beneficial effects are reduced compared to 15 Hz. The other peaks show the effects of changing the signal frequency and pulse width—lowering the frequency below 15 Hz or lowering the pulse width below 200 uS results in reduced effectiveness. The signals between 15-25 Hz, and 200-300 uS maintain about the same effectiveness in decreasing the hypotensive and bronchoconstrictive symptoms of anaphylaxis.

Conclusions that may be drawn from the above experimental data include: (1) That the airway constriction and hypotension caused by anaphylaxis in guinea pigs can be significantly reduced by applying appropriate electrical signals to the vagus nerve. (2) That signals from 15 Hz to 25 Hz, 200 uS to 300 uS, and 1.0V to 1.5V were equally effective. (3) That a 25 Hz, 200 μS, 1.25V signal applied to the vagus nerve, airway constriction due to anaphylaxis was reduced up to 68%. This effect has been repeated on several animals. (4) That the 25 Hz, 200 uS, 1.25V signal applied to the vagus nerve produces up to a 100% increase in blood pressure in an anaphylactic guinea pig experiencing severe hypotension. This effect has been repeated on several animals. This may have applications in the treatment of other low blood pressure conditions such as hypovolemia and septic shock. (5) That there is some evidence that the application of the signal to the vagus nerve may have the ability to shorten the duration of an anaphylactic episode.

Experimental Procedure 4

Additional test data were taken to demonstrate the present invention's results for treating septic and hypovolemic shock. When infection occurs due to sepsis, the body enlists a complex immunologic cascade to protect itself from microbial attack. This defense, if poorly regulated, can spiral out of control, leading to severe sepsis (acute organ dysfunction secondary to infection) and septic shock (severe sepsis plus hypotension not reversed with fluid resuscitation). If the latter occurs, widespread inflammation and blood clotting can cause a depletion of oxygen to tissues and organs, which can lead to multi-organ failure and death. Early signs of sepsis are an elevated heart rate, rapid breathing and abnormal temperature. The most common cause of sepsis is bacterial infection, but parasitic, viral and fungal infections can also lead to the problem.

The immunologic cascade involves many mechanisms, including the release of cytokines, the activation of neutrophils, monocytes, and microvascular endothelial cells. Neuroendocrine reflexes are also activated along with plasma protein cascade systems such as the complement system, the intrinsic (contact system) and extrinsic pathways of coagulation, and the fibrinolytic system. Macrophages are the first cells to come in contact with pathogens, and are thus key players in controlling the infection cascade. If stimulated for too long, the macrophage will release inflammatory mediators (TNFa, IL-1, and IL-6) that act synergistically to augment the inflammatory response.

Neutrophils are also involved in the inflammation cascade, producing proteases, cytokines, and toxic oxygen radicals to destroy bacteria. Due to the release of these substances, the capillary pores of damaged endothelial cells allow the leakage of certain large molecular plasma substances. These substances—including albumin, fibrinogen, some gamma globulins and platelets—pass into the interstitial tissue along with obligatory water and electrolytes. This phenomenon increases the "potential space" between cells and is called "third space". As a result, the cells are separated by a greater distance from functioning capillaries, which are the source of their oxygen supply (red blood cells within the capillaries), nutrients, and waste disposal transport. Pressure in the interstitial tissue is increased by this leakage causing compression of capillaries and lymph vessels with further dysfunction of the microcirculation. Edema or swelling is an obvious after-effect of this damaged microcirculation, which ultimately results in anasarca and multiple organ dysfunction and leads to multiple organ failure. Continued infusion of I.V. fluids are required to maintain adequate intravascular volume and blood pressure.

Due to the biophysical problems associated with the microvascular dysfunction, recovery time is greatly prolonged and many cells die in the effected tissue(s) due to the lack of oxygen and nutrients. Cellular and organ functions are compromised leading to the collapse of circulatory dynamics. This is a key underlying process in the development of systemic inflammatory response syndrome (SIRS), and multiple organ dysfunction syndrome (MODS), often proceeding to multiple organ failure (MOF) and even death.

Figure 22:
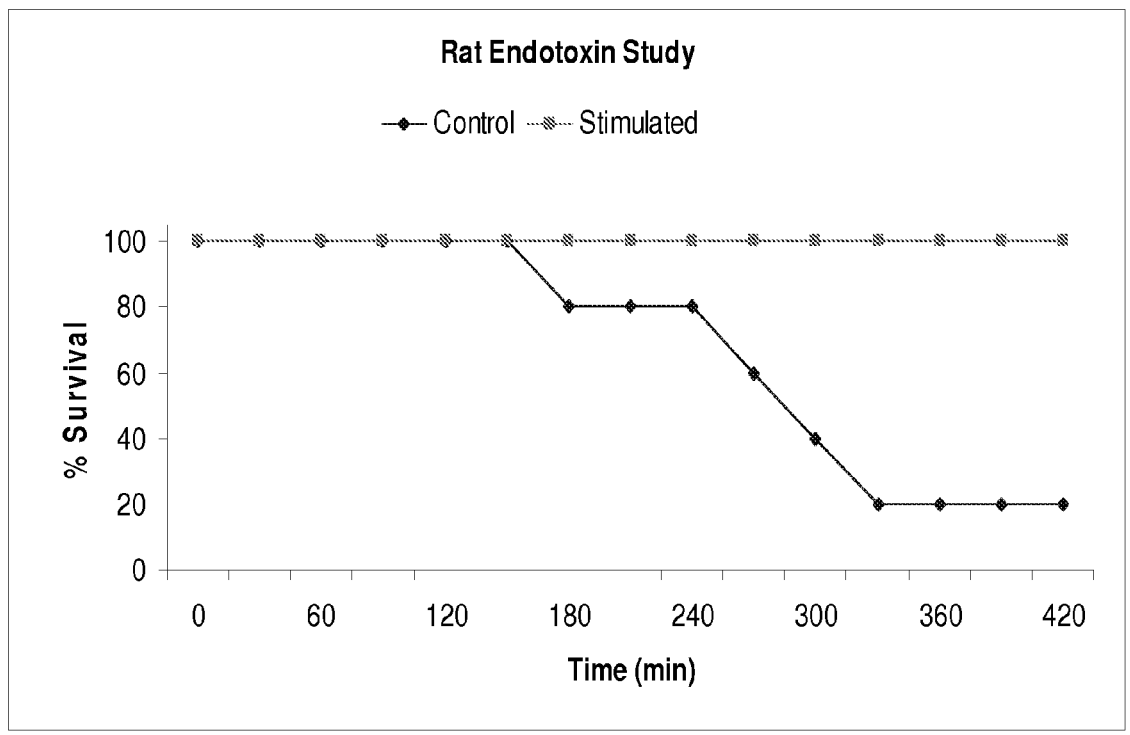
FIGS. 22-26 graphically illustrate exemplary experimental data obtained for the treatment of septic shock and hypovolemic shock according to the present invention.

FIG. 22 illustrates results from testing to determine whether electrical modulation according to the present invention may permit an animal suffering from septic shock to survive for a longer period of time. In these studies, ten rats were injected with a lethal 60 mg/kg intraperitoneal dose of *E. Coli* lipopolysaccharide to simulate septic shock. Five rats were treated with electrical stimulation according to the present invention (stimulated line in FIG. 22) and five rats were left alone (control line in FIG. 22). In the treated rats, a bipolar electrode was positioned on the right cervical vagus nerve and a 15 Hz, 300 microseconds, 0.22 volts signal was delivered to the electrode.

As shown, the control rats started to expire after three hours and four of them had expired in less than six hours. By contrast, all five rats that were treated with bipolar stimulation survived beyond seven hours. Thus, the treated rats had a significantly higher survival rate (100% versus 20%, p=0.02).

Figure 23:
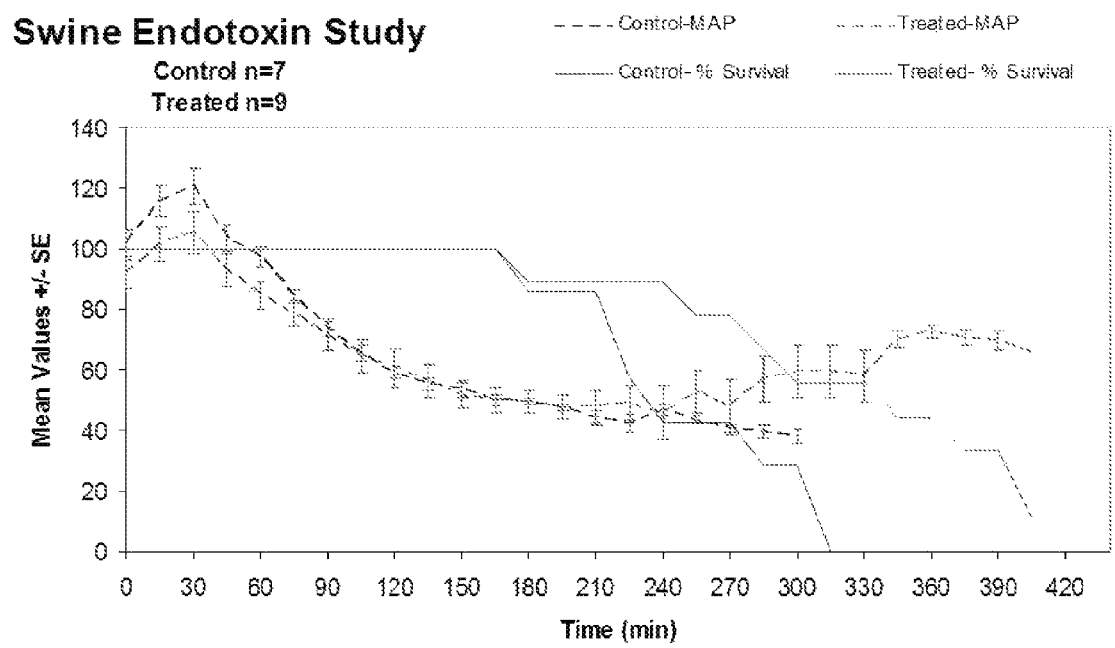
Figure 24:
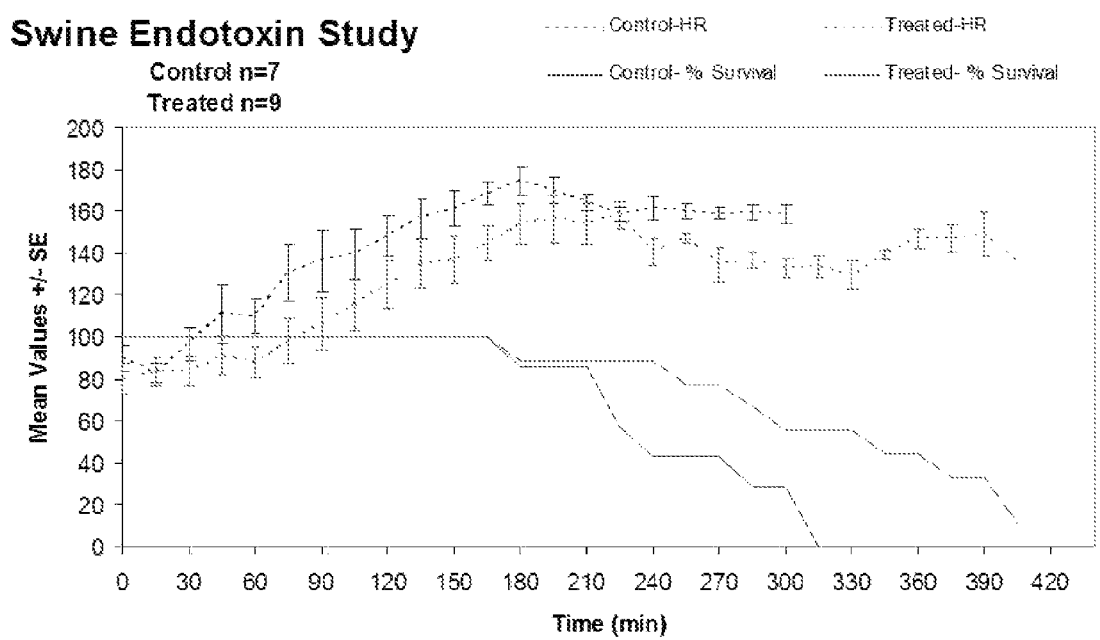

FIGS. 23 and 24 illustrate results from a swine endotoxin study. As with the guinea pigs in FIG. 22, sixteen pigs were injected with a lethal dose of *E. Coli* lipopolysaccharide at 2.5 mg iv bolus followed by continuous 1.5 mg/hr infusion to simulate the effects of septic shock. Seven pigs were left untreated with electrical stimulation and nine pigs were treated. In treated animals, an esophageal electrode (similar to the one described above) was inserted through the subject's esophagus to a depth corresponding with the cricoid notch. Saline was delivered to inflate the balloon and provide electrical contact between the electrode and the esophagus. An electrical impulse was then delivered to the electrode until study end. The electrical impulse had a frequency of 15 Hz, an amplitude of 5 volts and a pulse width of 300 microseconds.

FIG. 23 graphically illustrates survival timelines and mean arterial blood pressures for the treated and control animals. As shown, the control animals started to die at 180 minutes and by 315 minutes, all control animals had died. By contrast, the treated animals survived for a much longer period of time with over 50% of the treated animals surviving past 315 minutes. Similarly, mean arterial blood pressure for the treated animals remained substantially the same as the control animals after about 210 minutes.

FIG. 24 graphically illustrates the survival timelines and the heart rates of the treated and control animals. As shown, the heart rates for the treated animals remained lower than the heart rates for the control animals. Thus, the treated animals were able to maintain the same blood pressure as the control animals with lower heart rates. Applicant believes that this allowed the treated animals to avoid circulatory collapse and death for a longer period of time than the control animals.

Figure 25:
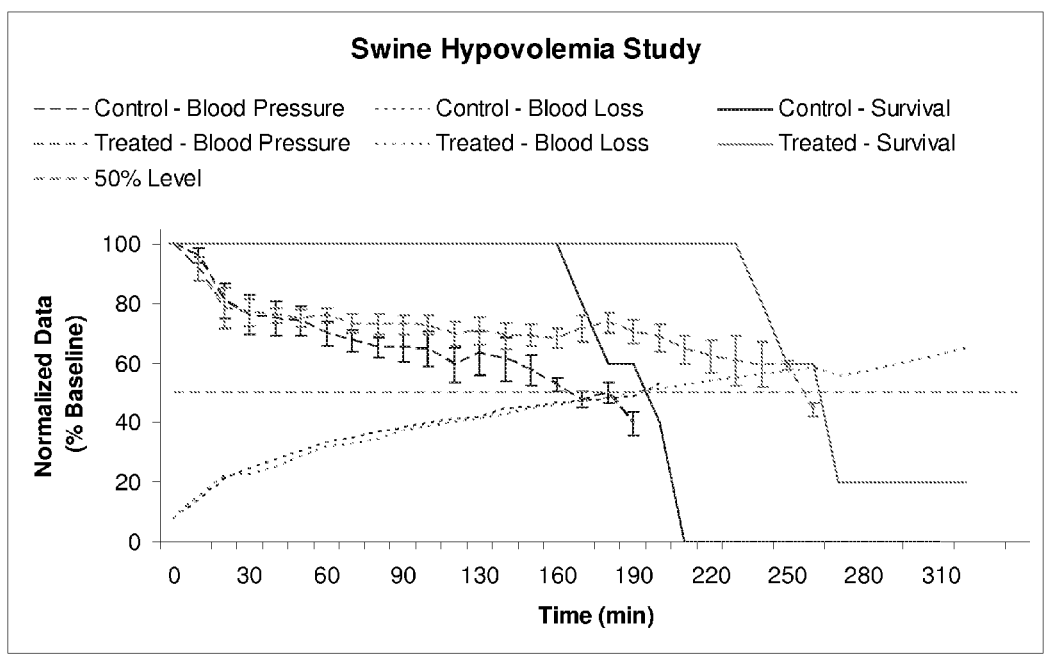
Figure 26:
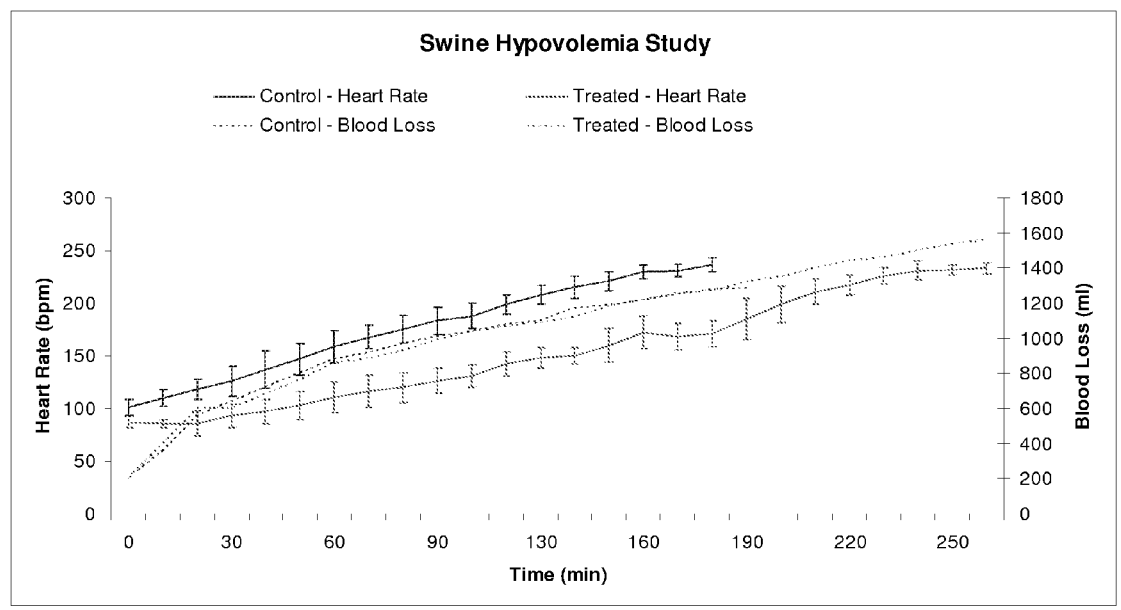

FIGS. 25 and 26 graphically illustrate results from a swine hypovolemia study. In this porcine hypovolemic model, blood was slowly withdrawn from five control and five stimulated animals while monitoring heart rate, blood pressure and survival. An esophageal balloon electrode (similar to those described above) was inserted orally through the subject's esophagus and positioned such that the balloon electrode was within or just under the cricoid notch. The balloon was inflated with about 5 ml of saline and an electrical impulse was applied to the electrode until study end. The electrical impulse had a frequency of 15 Hz a pulse width of 300 microseconds and an amplitude of about 5 volts.

In the control animals, a 50% blood loss corresponded to a near 50% decrease in blood pressure and proved lethal. By contrast, this blood loss was well tolerated in the treated animals. Further, animals receiving stimulation could withstand additional blood loss, up to 60%, before impacting blood pressure and survival.

As shown in FIG. 26, the heart rate for the treated animals in the hypovolemic model remained below the heart rate in the control animals. This effect occurred almost immediately and lasted throughout the duration of the study. Thus, similar to the sepsis study above, the treated animals were able to maintain the same or slightly higher blood pressure at a lower heart rate than the control animals. This appears to be the primary reason that the treated animals survived longer despite suffering more blood loss than the control animals.

The sepsis and hypovolemia studies shown in FIGS. 23-26 did not investigate the actual physiological mechanism that resulted in death. Blood pressure is the combined product of vascular compliance and heart function. As the blood pressure falls, the body increases the cardiac output through changes in inotropic and chronotropic contractions. During circulatory collapse, where cardiac refill is inadequate, cardiac output is reduced and cannot compensate for the drop in blood pressure. While this can lead to death through inadequate cerebral perfusion and organ failure, it may be that the inadequate cardiac perfusion results in myocardial hypoxia and heart failure as the cause of death. Thus, stimulation, by maintaining blood pressure and adequate cardiac refill at lower heart rates, could enable the heart to provide adequate myocardial perfusion and improved survival.

Figure 27:
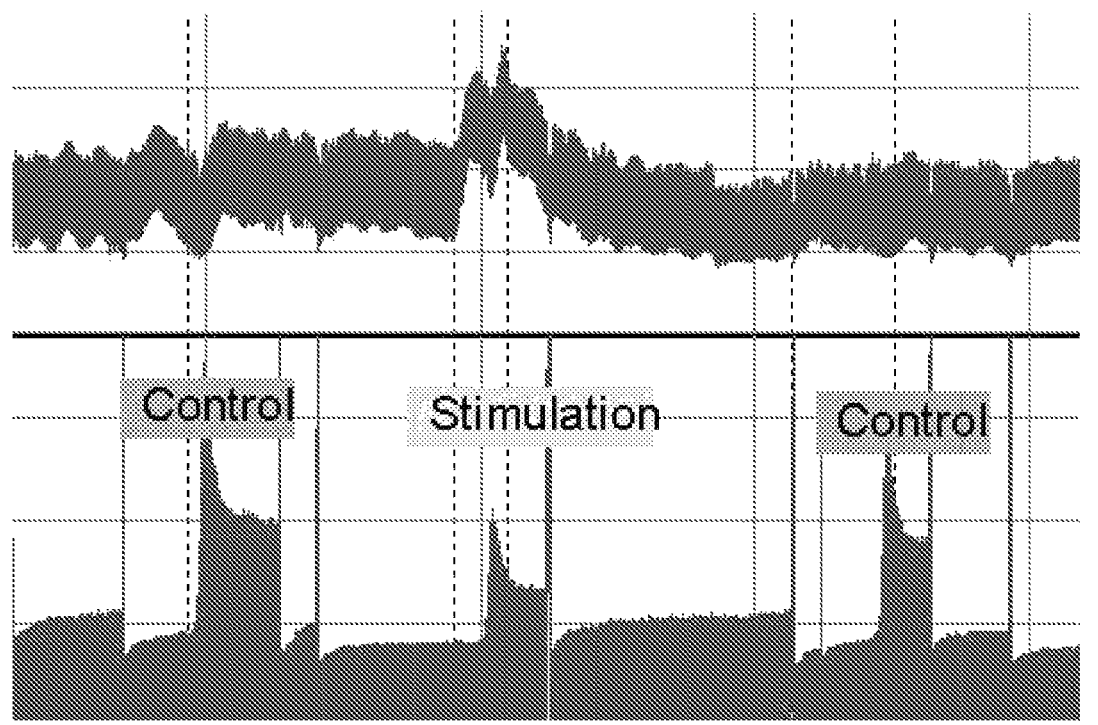
FIGS. 27 and 28 graphically illustrate exemplary experimental data with afferent nerve blocking to illustrate the mechanism of action of the present invention.
Figure 28:
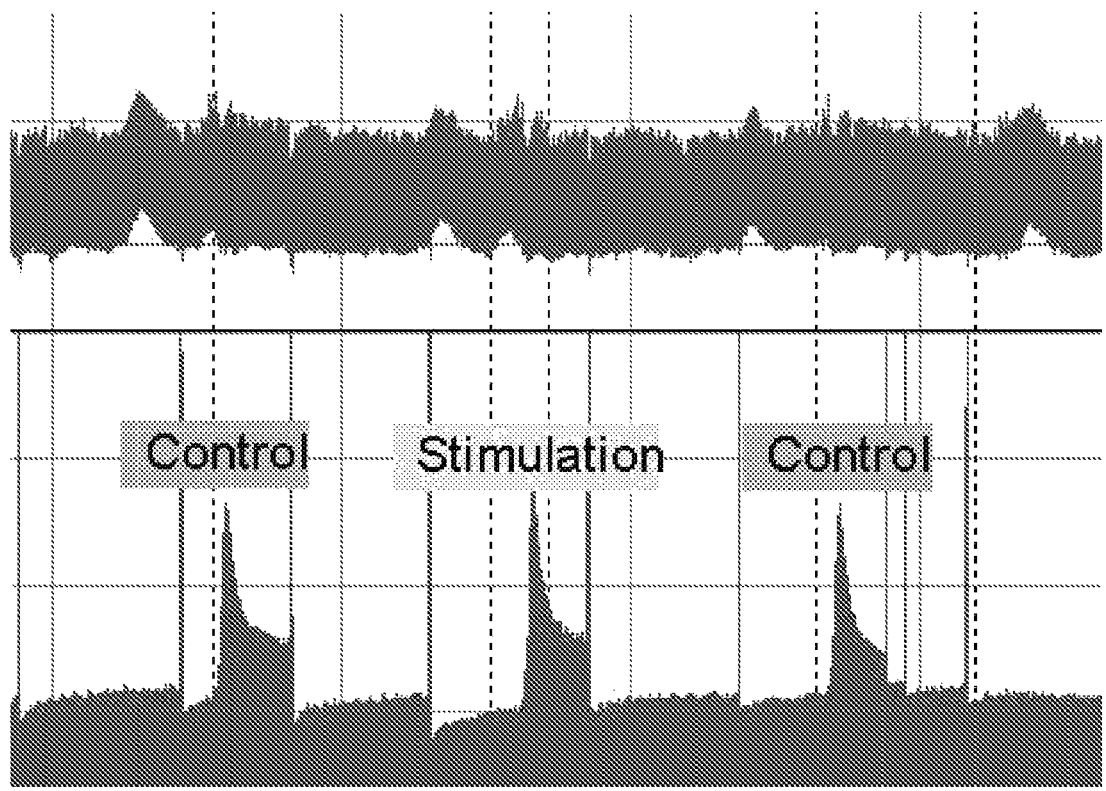

FIGS. 27-28 illustrate experimental test data on guinea pigs to demonstrate the mechanism of action of applicant's invention (i.e., by tying off the vagal nerves rostral or proximal of the electrodes). As shown in FIGS. 27 and 28, applicant performed tests on male guinea pigs (400 g) with similar conditions as the tests described above in FIGS. 4-12. The guinea pigs were prepared and both vagus nerves were exposed in the neck and connected to electrodes to allow selective stimuli of these nerves. Following 15 minutes of stabilization, baseline hemodynamic and airway pressure measurements were made before and after the administration of repetitive doses of i.v. histamine. Following the establishment of a consistent response to i.v. histamine, vagal nerve stimulation was attempted similar to that described above.

FIG. 27 illustrates the results of the experiment before tying off the vagal nerves rostral of the electrodes. The first and third peaks on the lower green lines illustrate the control (no stimulation) and the second or middle peak illustrate stimulation according to the present invention. As shown, electrical stimulation caused both an increase in blood pressure (red lines) and a decrease in bronchoconstriction (green lines). This corresponds with earlier experiments discussed above.

FIG. 28 illustrates the results of the same experiment except that the vagal nerves are tied off rostral of the electrodes. This prevents any response by the afferent nerves leading to the brain while allowing response by the efferent nerves. As shown, the blood pressure remained the same as the control during electrical stimulation. Similarly, the bronchoconstriction peak remained the same as well. Thus, electrical stimulation had no effect on either blood pressure or bronchoconstriction when the afferent nerves were tied off. This demonstrates that the electrical stimulation modulated the afferent nerves of the parasympathetic nervous system without substantially modulating the efferent nerves in the same region of the parasympathetic nervous system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating bronchoconstriction in a patient comprising applying at least one electrical impulse to at least one selected region of a parasympathetic nervous system of the patient, the electrical impulse being sufficient to modulate one or more afferent nerves in a selected region of the parasympathetic nervous system such to relax bronchial smooth muscle in the patient.

2. The method set forth in claim 1 wherein the electrical impulse is sufficient to stimulate the afferent nerves in the selected region of the parasympathetic nervous system.

3. The method set forth in claim 1 wherein the electrical impulse is insufficient to substantially modulate the efferent nerves in the selected region of the parasympathetic nervous system.

4. The method set forth in claim 2 wherein the electrical impulse is sufficient to cause the afferent nerves in the selected region to modulate one or more nerves in a sympathetic nervous system.

5. The method set forth in claim 4 wherein the afferent nerves in the selected region cause an increase in activity of the one or more nerves of the sympathetic nervous system.

6. The method set forth in claim 1 further comprising the step of positioning an electrode adjacent to or near the selected region of the parasympathetic nervous system and applying an electrical signal having an amplitude to the electrode; wherein a distance between the electrode and the selected region and the amplitude are selected such that the electrical signal modulates the afferent nerves at the selected region of the parasympathetic nervous system without substantially modulating the efferent nerves at the selected region of the parasympathetic nervous system.

7. The method of claim 6 wherein the amplitude is less than 12 volts.

8. The method of claim 1 wherein the electrical impulse is sufficient to relax bronchial smooth muscle and maintain a substantially stable heart rate.

9. The method of claim 1 wherein the electrical impulse has a frequency of about 10 Hz to 100 Hz.

10. The method of claim 1 wherein the electrical impulse has a frequency of about 15-35 Hz, a pulsed on-time of about 100-400 microseconds, and an amplitude of about 0.1 to 2 volts.

11. A method of treating bronchoconstriction in a patient comprising applying at least one electrical impulse to at least one selected region of a vagus nerve of the patient, the electrical impulse being sufficient to modulate one or more afferent nerves in a selected region of the vagus nerve.

12. The method of claim 11 wherein the applying step is carried out by positioning an electrode near or adjacent to a cricoid cartilage of the patient and applying the electrical impulse to the electrode.

13. The method of claim 11 wherein the applying step is carried out by positioning an electrode adjacent to or on a neck of the patient and applying the electrical impulse to the electrode.

14. The method of claim 11 wherein the electrical impulse is sufficient to stimulate the afferent nerves in the selected region of the vagus nerve.

15. The method of claim 11 wherein the electrical impulse is insufficient to substantially modulate the efferent nerves of the selected region of the vagus nerve.

16. The method of claim 11 wherein the electrical impulse is sufficient to cause the afferent nerves to cause an increase in activity of one or more nerves in a sympathetic nervous system of the patient responsible to effect a dilation of bronchial smooth muscle.

17. The method of claim 13 wherein the electrical impulse to applied transcutaneously through an outer skin surface of the patient's neck to the vagus nerve.

* * * * *